US005965126A

United States Patent [19]
Pegg et al.

[11] Patent Number: 5,965,126
[45] Date of Patent: Oct. 12, 1999

[54] USE OF MUTANT ALKYLTRANSFERASES FOR GENE THERAPY TO PROTECT FROM TOXICITY OF THERAPEUTIC ALKYLATING AGENTS

[75] Inventors: Anthony E. Pegg, Hershey, Pa.; Stanton L. Gerson, Pepperpike, Ohio

[73] Assignee: The Penn State Research Foundation, University Park, Pa.

[21] Appl. No.: 08/620,969

[22] Filed: Mar. 25, 1996

[51] Int. Cl.⁶ ..................................................... A01N 63/00
[52] U.S. Cl. .......................... 424/93.21; 514/44; 435/455; 435/325; 435/320.1; 435/69.5; 536/23.1
[58] Field of Search ........................... 514/44; 424/93.21; 435/172.3, 240.2, 69.5, 325, 455, 320.1; 935/62, 57; 536/23.1

[56] References Cited

U.S. PATENT DOCUMENTS

| | | | |
|---|---|---|---|
| 5,091,430 | 2/1992 | Moschel et al. | 514/262 |
| 5,352,669 | 10/1994 | Moschel et al. | 514/45 |
| 5,358,952 | 10/1994 | Moschel et al. | 514/262 |
| 5,637,483 | 6/1997 | Dranoff et al. | 424/93.21 |

FOREIGN PATENT DOCUMENTS

WO 92/07943  2/1992  WIPO .

OTHER PUBLICATIONS

Allay, et al., 1995, Blood 85 (11): 3342–3351.
Moritz, et al., 1995, Can. Res., 55: 2608–2614.
Dolan, et al., 1994, Can. Res. 54: 5123–5130.
Crone, et al., 1995, Carcinogenesis 16 (8): 1687–1692.
Crone and Pegg, 1993, Can. Res. 53: 4750–4753.
Crone, et al., 1994, Can Res. 54: 6221–6227.
Pegg, et al., 1995, Biochem. Pharmacol. 50 (8): 1141–1148.
Gerson, et al., 1994, Mutation Res. 307: 541–555.
Dolan, et al., Can. Chemother Pharmacol. 35: 121–126.
Brody and Crystal, 1994, Ann NY Acad. Sci. 716: 90–103.
Dunbar, et al., 1993, Hum. Gene Ther. 4: 205–22.
Hawley, 1994, Ann NY Acad. Sci. 716: 327–330.
Cassel, et al., 1993, Exp. Hematol. 21: 585–591.
Sekhar, et al., 1996, Hum Gene Ther. 7: 33–38.
Dunbar, et al., 1994, Ann NY Acad. Sci 716: 216–227.
Dick, et al., 1991, Blood 78 (3): 624–634.
Huber and Lazo, 1994, Ann NY Acad. Sci. 716: 1–11.
Kotani, et al., 1994, Hum. Gene Ther. 5: 19–28.
Harris, et al., 1995, Proc. Amer. Assoc. Can Res. 36: 419.
Larochelle et al. Nature Medicine, 1995, vol. 2, 12:1329–1337.
Morrison et al. Nature Medicine, 1995, vol. 2, 12:1282.
Beusechem et al. Human Gene Therapy 1996, 7:1649–1668.
Banerjee et al. Stem Cells 1994, 12:378–385.
Karlsson. Blood 1991, vol. 78, 10:2481–2491.
Dolan (Adv. Drug Delivery Rev., 1997, 26, 2, 3:105–118).
Ngo et al., in The Protein Folding Problem and Tertiary Structure Prediction, 1994, Merz et al., (ed.), Birkhauser, Boston, MA, pp. 433 and 492–495).
Mastrangelo et al. (Seminars in Oncology, vol. 23, No. 1:4–21, 1996).
Stein J., ed., 1993 in: Internal Medicine, 4th edition, Mosby Year Book, pp. 699–715.
Gerson et al., Proc. Amer. Assoc. Cancer Res., vol. 35, Mar. 1994, p. 699.
Ronald Crystal, Science, vol. 270, 1995, pp. 404–410.
Crone et al. (Cancer Res., 54, 6221–6227, 1994).
Reese et al. (Proc. Amer. Assoc. Cancer Res., vol. 37, Mar. 1996, p. 334).
Marathi et al. (Proc. Amer. Ass. Cancer Res., Mar. 1995, vol. 36, p. 419).
Huber et al. (Annals New York Aca. Sci., vol. 716, 1994:6–12).

*Primary Examiner*—Bruce R. Campbell
*Assistant Examiner*—Dave Trong Nguyen
*Attorney, Agent, or Firm*—Thomas J. Monahan

[57] ABSTRACT

The present invention relates to methods of treating neoplastic disease whereby gene therapy treatments are employed in combination with a chemotherapy regime. A combinational therapy with anti-neoplastic alkylating agents will optimize host tumor sensitivity to these agents used alone or in combination with $O^6$-benzylguanine (BG) or a similar compound or compounds. Hematopoietic cells are infected with a transgene expressing a mutant AGT protein exhibiting DNA repair activity while imparting resistance to BG or a related compound. Introduction of the transduced hematopoietic cell population expressing the mutant AGT protein into the patient in tandem with the chemotherapeutic regime will substantially reduce myelosuppression traditionally associated with the administration of these anti-neoplastic drugs.

9 Claims, 8 Drawing Sheets

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (ii) MOLECULE TYPE: oligonucleotide (iii) HYPOTHETICAL: NO (iv) ANTI-SENSE: NO (xi) SEQUENCE DESCRIPTION: SEQ ID NO:1:

CTCACTATAG GATCCAAAAT GGACAAGGAT                                  30

(2) INFORMATION FOR SEQ ID NO:2:

(i) SEQUENCE CHARACTERISTICS:
       (A) LENGTH: 28 base pairs
       (B) TYPE: nucleic acid
       (C) STRANDEDNESS: single
       (D) TOPOLOGY: linear (ii) MOLECULE TYPE: oligonucleotide (iii) HYPOTHETICAL: NO (iv) ANTI-SENSE: NO (xi) SEQUENCE DESCRIPTION: SEQ ID NO:2:

CTTGGAACCA TGGACAAGGA TTGTGAAA                                    28

(2) INFORMATION FOR SEQ ID NO:3:

(i) SEQUENCE CHARACTERISTICS:
       (A) LENGTH: 31 base pairs
       (B) TYPE: nucleic acid
       (C) STRANDEDNESS: single
       (D) TOPOLOGY: linear (ii) MOLECULE TYPE: oligonucleotide (iii) HYPOTHETICAL: NO (iv) ANTI-SENSE: NO (xi) SEQUENCE DESCRIPTION: SEQ ID NO:3:

CTTAGGATCC CATCCGATGC AGTGTTACAC G                                31

(2) INFORMATION FOR SEQ ID NO:4:

(i) SEQUENCE CHARACTERISTICS:
       (A) LENGTH: 27 base pairs
       (B) TYPE: nucleic acid
       (C) STRANDEDNESS: single
       (D) TOPOLOGY: linear (ii) MOLECULE TYPE: oligonucleotide (iii) HYPOTHETICAL: NO (iv) ANTI-SENSE: NO (xi) SEQUENCE DESCRIPTION: SEQ ID NO:4:

```
AGCGGAGCCG TGGCCAACTA CTCCGGA                                              27

(2) INFORMATION FOR SEQ ID NO:5:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: oligonucleotide (iii) HYPOTHETICAL: NO (iv) ANTI-SENSE: NO (xi) SEQUENCE DESCRIPTION: SEQ ID NO:5:

TCCGGAGTAG TTGGCCACGG CTCCGCTG                                             28

(2) INFORMATION FOR SEQ ID NO:6:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: oligonucleotide (iii) HYPOTHETICAL: NO (iv) ANTI-SENSE: NO (xi) SEQUENCE DESCRIPTION: SEQ ID NO:6:

TGGTACCTCA CCCTTACCGA GTC                                                  23

(2) INFORMATION FOR SEQ ID NO:7:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: oligonucleotide (iii) HYPOTHETICAL: NO (iv) ANTI-SENSE: NO (xi) SEQUENCE DESCRIPTION: SEQ ID NO:7:

ACACCTGTCT GGTGAACGAC TCT                                                  23
```

USE OF MUTANT ALKYLTRANSFERASES FOR GENE THERAPY TO PROTECT FROM TOXICITY OF THERAPEUTIC ALKYLATING AGENTS

1. INTRODUCTION

The present invention relates to methods of treating neoplastic disease whereby gene therapy treatments are employed in combination with a chemotherapy regime. More specifically, this combinational therapy will optimize host tumor sensitivity to alkylating and methylating agents used alone or in combination with $O^6$-benzylguanine (BG) or a similar compound or compounds. BG inhibits wild type human $O^6$-alkylguanine-DNA alkyltransferase (AGT), a DNA repair protein known to obviate the anti-neoplastic effects of alkylating agents. Hematopoietic cells are infected with a transgene expressing a mutant AGT protein exhibiting DNA repair activity while imparting resistance to BG or a related compound. Introduction of the transduced hematopoietic cell population expressing the mutant AGT protein into the patient in tandem with the chemotherapeutic regime will substantially reduce myelosuppression traditionally associated with the administration of these anti-neoplastic drugs.

The present invention also includes methods of dominant selection of a second transduced gene in hematopoietic cells wherein a first transduced gene expressing an AGT mutant resistant to an $O^6$-benzylated guanine derivative is co-cultured in the presence of the $O^6$-benzylated guanine derivative and an alkylating or methylating agent. A marked enhancement of clonogenic survival of $CD34^+$ cells transduced with the transgene expressing G156A AGT in the presence of BG and BCNU shows that any AGT mutant showing similar activity will be useful as a drug resistance gene.

2. BACKGROUND OF THE INVENTION

Alkylating and methylating agents are important groups of compounds for use in cancer chemotherapy. Chloroethylating agents, including but not limited to chloroethylnitrosoureas, form DNA adducts within the cell nucleus that promote alterations in DNA structure and/or function. These changes at the DNA level lead to cytotoxicity within the targeted cell.

Chloroethylnitrosoureas such as BCNU (N,N'-bis(2-cholorethyl)-N-nitrosourea) and CCNU (N-(2-cholorethyl)-3-cyclohexyl-N-nitrosourea) are lipid soluble compounds that have been shown to possess clinical utility against some neoplasms but with limited success in clinical trials. These chloroethylnitrosoureas promote DNA alkylation at the $O^6$ position of guanine, leading to DNA interstrand crosslinking and altered fidelity of DNA replication and transcription. This induced interstrand crosslinking involves formation of a chloroethyl adduct at the guanine residue that undergoes an intramolecular rearrangement to produce an unstable intermediate that reacts with the cross strand cytosine residue. The result is a $N^1$-guanine, $N^3$-cytosine-ethanol crosslink.

This $N^1$-guanine, $N^3$-cytosine-ethanol crosslink can be prevented by the DNA repair protein, $O^6$-alkylguanine-DNA alkyltransferase (AGT). This repair protein is active in mammalian tumor cells and is responsible for protecting cells from the antitumor effects normally associated with chloroethylating agents such as BCNU and CCNU. AGT has a unique mechanism of action in that it brings about the transfer of alkyl groups present on the $O^6$ position of guanine in DNA to a cysteine residue located within the AGT amino acid sequence (Lindahl, et al., 1988, *Annu. Rev. Biochem.* 57: 133–157; Pegg, 1990, *Cancer Res.* 50: 6119–6129). The resulting S-alkylcysteine-containing AGT protein is not converted back to cysteine. AGT acts only once and the number of $O^6$-alkylguanine residues that can be repaired is equal to the number of available AGT molecules. Therefore, tumor cells expressing high levels of AGT show resistance to alkylating and methylating chemotherapeutic drugs, which may limit clinical effectiveness of these agents. To this end, a reduction of functional AGT in mammalian tumor cells should correlate to increased sensitivity of these cells to the chemotherapeutic effects of chloroethylating agents that form DNA adducts at the $O^6$ position of guanine.

U.S. Pat. No. 5,091,430, issued to Moschel, et al. on Feb. 24, 1992 discloses $O^6$-substituted guanine compounds which inhibit AGT. An exemplified compound which inhibits AGT is $O^6$-benzylguanine (BG). It has been shown that BG is a strong time and concentration dependent inactivator of human AGT (Dolan, et al., 1990, *Proc. Natl. Acad. Sci.* 87: 686–690). This mechanism has been confirmed by the identification of S-benzylcysteine in AGT and the formation of stoichiometric amounts of guanine following incubation with BG.

U.S. Pat. No. 5,352,669 issued to Moschel, et al. on Oct. 4, 1994 discloses $O^6$-substituted guanosine and 2' deoxyguanosine compounds which are shown to inhibit AGT.

U.S. Pat. No. 5,358,952 issued to Moschel, et al. on Oct. 22, 1994 disclose pharmaceutical combinations for chemotherapy comprising $O^6$-substituted guanine compounds in tandem with anti-neoplastic alkylating agents.

A major limitation in the use of alkylating and methylating agents in the treatment of neoplastic disease is the profound myelosuppression produced by these drugs. This problem peaks at about 4–6 weeks after treatment and thus prevents the repetition of cyclic therapy at preferred intervals. This myelosuppression is due to low concentrations of AGT in hematopoietic cells.

Crone and Pegg (1993, *Cancer Res.* 53: 4750–4753) disclose a mutant human AGT protein with a single amino acid change of proline to alanine at aa #140 (P140A). This mutant human AGT shows a decrease in sensitivity to BG in vitro. The authors do not address in vivo activity of this mutant in regard to BG or BG/BCNU combinations.

Crone, et al. (1994, *Cancer Res.* 54: 6221–6227) disclose an additional mutant human AGT protein with a single amino acid change of glycine to alanine at aa #156 (G156A). As with human AGT P140A, G156A shows a decrease in sensitivity to BG in vitro. Again, the authors do not address in vivo activity of this mutant in regard to BG or BG/BCNU combinations.

Gerson, et al. (1994, *Mutation Res.* 307:541–555) disclose transgenic mice expressing either the wild type human $O^6$-methylguanine-DNA methyltransferase (MGMT) cDNA or the bacterial ada gene (which expresses a prokaryotic version of AGT resistant to BG). The authors show a level of protection against addition of BCNU in transformed cell types shown to express the respective gene.

Another avenue of addressing alkylating agent toxicity is gene therapy. Moritz, et al. (1995, *Cancer Res.* 55:2608–2614) disclose retroviral mediated expression of MGMT in murine bone marrow cells. The authors used a strong promoter in attempts to overexpress MGMT in the cells in an effort to overcome the effect of added BCNU for in vitro and in vivo studies. No attempt was made nor suggested by the authors to inhibit MGMT at the tumor site and provide a resistant form of the protein in hematopoietic cells to reduce BCNU-induced myelosuppression. Allay, et al. (1995, *Blood* 85: 3342–3351) also show retroviral mediated expression of MGMT in murine bone marrow cells. The authors used the MPSV vector with the 5'LTR promoter fragment to increase expression of MGMT and also obtain in vitro reduction in BCNU-induced myelosuppression. Harris, et al. (1995, *Proc. Amer. Assoc. Can. Res.* 36: 419) disclose retroviral mediated expression of a bacterial ada gene and a measure of resistance to nitrosoureas. The authors noted increased resistance to BG and BCNU in vivo. Maze, et al. (1996, *Proc. Natl. Acad. Sci.* 93: 206–210) disclose in vitro and in vivo expression of wtMGMT in mouse bone marrow cells. These authors do not suggest inhibition of MGMT at the tumor site and providing a human resistant form of the protein in hematopoietic cells to reduce BCNU-induced myelosuppression. These studies lack an efficient gene therapy application at the clinical level since the routine high level expression of AGT in these cells is difficult to accomplish and even substantial increases in alkyltransferase may not be sufficient to render these cells less susceptible to killing than many of the tumors which are being treated since these tumors may have high levels of alkyltransferase. Although MGMT overexpression increases BCNU resistance in normal murine and human hematopoitic cells, the effect has been quite modest, leaving serious questions about any therapeutic utility for these applications. Therefore, a fundamental problem exists in relation to overexpression of human AGT in hematopoietic cells in an attempt to overcome sensitivity to chloroethylating compounds targeted to tumor cells.

Although AGT P140A and G156A show resistance to BG and no apparent defect in the ability to repair $O^6$-methylguanine in DNA in vitro, the rate of repair of methylated DNA is very rapid and is difficult to measure accurately under physiological conditions. Also, it is not known whether the ability to act on the larger 2-chloroethyl group is affected by these mutations. Furthermore, some point mutations in AGT have a pronounced destabilizing effect and may reduce the steady state level of the AGT protein. These factors could limit the ability of the mutant AGTs to protect cells from chloroethylation. Therefore, it is possible that some or all of these mutations do also affect the ability to repair $O^6$-(2-chloroethyl)guanine in cellular DNA and would therefore not produce resistance to sensitization by BG.

Therefore, despite attempts to overcome the extreme myelosuppression observed with the use of alkylating and methylating agents in chemotherapy regimes, a need exists for improved methods of using these anti-neoplastic agents to treat various neoplastic diseases.

3. SUMMARY OF THE INVENTION

The present invention overcomes a major limitation in the use of methylating and alkylating agents in the treatment of neoplastic disease by addressing the problem of extreme myelosuppression produced by these drugs. Therefore, this specification discloses gene therapy treatments to improve chemotherapeutic treatments of a neoplastic disease.

The present invention relates to methods of optimizing a chemotherapeutic regime whereby a compound of the regime selectively inhibits a tumor cell-localized wild type protein while a mutant version of this protein, resistant to the compound, is simultaneously provided in hematopoietic cells. This mutated version of the protein also exhibits DNA repair activity. These methods require transducing a population of hematopoietic cells with a transgenic construction expressing the mutant protein and reintroducing the transduced cells into the mammalian host so as to promote expression of the mutant protein in bone marrow cells during the respective chemotherapy regime.

To this end, a portion of the invention relates to use of these gene therapy treatments to improve a chemotherapeutic regime wherein $O^6$-benzylguanine (BG) is added to render tumor cells containing high levels of $O^6$-alkylguanine-DNA alkyltransferase (AGT) sensitive to chloroethylating agents. In this application a mutated nucleic acid sequence is generated which expresses an AGT DNA repair protein resistant to BG while retaining the ability to repair DNA adducts formed after exposure to various chloroethylating agents. The transduction and expression of such an AGT mutant gene in hematopoietic cells followed by reintroduction of the transduced cells into the mammalian host will result in a relevant cell population which both shows an elevated level of the mutant AGT and in turn is not sensitive to the presence of BG as a chemotherapeutic agent. In other words, expression of the mutant AGT protein overcomes the effect of a chloroethylating agent not only through elevated concentrations of the protein but also due to resistance to BG. In contrast, BG inhibits tumor cell localized wild type AGT, preventing repair of DNA adducts generated in the tumor cell genome through the action of a respective chloroethylating agent.

It is contemplated in the present invention that a transgenic construct of interest be delivered to hematopoietic cells by viral-mediated means. Recombinant virus vectors utilized in the present invention include, but are not limited to (a) retroviral vectors, including but not limited to vectors derived from a Moloney murine leukemia virus (MoMLV) or a myeloproliferative sarcoma virus (MPSV); (b) adenovirus vectors; (c) adeno-associated vectors; (d) herpes simplex virus vectors; (e) SV40 vectors; (f) polyoma virus vectors; (g) papilloma virus vectors; (h) picornavirus vectors; and, (i) vaccinia virus vectors. Depending on the virus vector system chosen, techniques available to the skilled artisan are utilized to infect the target cell of choice with the recombinant virus vector.

In a specific embodiment of the present invention a transgenic construct of interest is subcloned into the retroviral vector MFG. This recombinant MFG retroviral vector is transferred into a packaging cell line and the recovered viral particles are used to transfect a mammalian cell population line, including but not limited to (1) peripheral blood mononuclear cell populations, preferably enriched for CD34$^+$ progenitors, and (2) bone marrow cell populations containing hematopoietic progenitor cells, preferably enriched for CD34$^+$ progenitors. The in vitro transfected cell populations are then reintroduced into the patient by known techniques.

In a specific embodiment of the present invention gene therapy treatments disclosed within this specification are utilized in tandem with a chemotherapeutic regime comprising BG and the chloroethylating agent N,N'-bis(2-cholorethyl)-N-nitrosourea (BCNU).

A specific embodiment of the invention regarding optimization of a chemotherapy regime including a chloroethylating agent in tandem with BG involves use of the human AGT mutant P140A, wherein proline #140 has been substituted with alanine.

Another specific embodiment of the invention regarding optimization of a chemotherapy regime including a chloroethylating agent in tandem with BG involves use of the human AGT mutant G156A, wherein glycine #156 has been substituted with alanine.

In another embodiment of the invention the human AGT mutant P140A may be subcloned in a MFG retroviral vector, thus generating a MFG-hAGT/P140A recombinant retroviral vector for transduction into hematopoietic cells and reintroduction into the patient as part of the chemotherapeutic regime comprising at least a compound which P140A AGT shows resistance as well as an alkylating or methylating agent used in the treatment of a neoplastic disease.

In a preferred embodiment of the invention the human AGT mutant P140A may be subcloned in a MFG retroviral vector, thus generating a MFG-hAGT/P140A recombinant retroviral vector for transduction into hematopoietic cells and reintroduction into the patient as part of the chemotherapeutic regime utilized in tandem with a chemotherapeutic regime comprising BG and the chloroethylating agent N,N'-bis(2-cholorethyl)-N-nitrosourea (BCNU).

In a preferred embodiment of the invention the human AGT mutant G156A may be subcloned in a MFG retroviral vector, thus generating a MFG-hAGT/G156A-based recombinant vector which is exemplified in Example Section 7 and referred throughout this specification simply as MFG-ΔMGMT, or ΔMGMT. This recombinant retroviral vector is then transduced into hematopoietic cells where selected transduced cells are reintroduced into the patient as part of the chemotherapeutic regime comprising at least a compound to which G156A AGT shows resistance as well as an alkylating or methylating agent used in the treatment of a neoplastic disease.

In an especially preferred embodiment of the invention the human AGT mutant G156A may be subcloned in a MFG retroviral vector, thus generating MFG-ΔMGMT (ΔMGMT) for transduction into hematopoietic cells and reintroduction into the patient as part of the chemotherapeutic regime utilized in tandem with a chemotherapeutic regime comprising BG and the chloroethylating agent N,N'-bis(2-cholorethyl)-N-nitrosourea (BCNU). Again, this MFG-hAGT/G156A based recombinant retroviral vector is exemplified in Example Section 7 and is referred to throughout this specification as MFG-ΔMGMT.

The present invention also includes methods of dominant selection of a second transduced gene in hematopoietic cells wherein a first transduced gene expressing an AGT mutant resistant to an $O^6$-benzylated guanine derivative is co-cultured in the presence of the $O^6$-benzylated guanine derivative and an alkylating or methylating agent. A marked enhancement of clonogenic survival of CD34$^+$ cells transduced with the transgene expressing G156A AGT in the presence of BG and BCNU shows that any AGT mutant showing similar activity will be useful as a drug resistance gene.

It is an object of the present invention to improve existing chemotherapeutic regimes which utilize methylating and chloroethylating agents to treat neoplastic diseases by incorporating gene therapy applications so as to overcome the inherent problem of myelosuppression associated with these compounds.

It is a further object of this invention to provide mutant human AGT sequences for transduction into relevant hematopoietic precursors for introduction or reintroduction into the host so as to substantially alleviate known problems of myelosuppression associated with the use of methylating and chloroethylating agents in chemotherapy of neoplastic diseases.

It is yet a further object of the invention to utilize mutant human AGTs P140A and/or G156A for transduction into relevant hematopoietic precursors for introduction or reintroduction into the host so as to substantially alleviate known problems of myelosuppression associated with the use of methylating and chloroethylating agents in chemotherapy of neoplastic diseases.

It is also an object of the present invention to provide an improved drug resistant based selection system for selecting a second therapeutic gene wherein a vector such as a MFG-based retroviral vector is tranduced into a population of target cells such that a first vector-based gene expresses an AGT mutant resistant to an $O^6$-benzylated guanine derivative is co-cultured in the presence of the $O^6$-benzylated guanine derivative and an alkylating or methylating agent. Such a drug selection system will allow for enhanced selection of cells expressing the second therapeutic gene.

These and other objects of the invention will be more fully understood from the following description of the invention, the figures, and the claims appended hereto.

3.1. DEFINITIONS

| | |
|---|---|
| BCNU | N,N'-bis(2-cholorethyl)-N-nitrosourea |
| CCNU | N-(2-cholorethyl)-3-cyclohexyl-N-nitrosourea |
| AGT | $O^6$-alkylguanine-DNA alkyltransferase |
| BG | $O^6$-benzylguanine |
| MPSV | myeloproliferative sarcoma virus |
| MoMLV | moloney murine leukemia virus |
| SDS-PAGE | SDS polyacrylamide gel electrophoresis |
| MGMT | $O^6$-methylguanine-DNA methyltransferase |

As used herein, the term "MGMT" denotes a gene or cDNA construct which encodes $O^6$-alkylguanine-DNA alkyltransferase (AGT). The term "MGMT" may be used interchangeably with "AGT" to denote such a nucleic acid sequence expressing a wild type or mutant version of the human AGT protein.

As used herein, the term "patient" includes members of the animal kingdom including but not limited to human beings.

As used herein, the term "mammalian host" includes members of the animal kingdom including but not limited to human beings.

4. BRIEF DESCRIPTION OF THE FIGURES

FIG. 1 shows Western blot analysis of AGT protein expression in CHO cells. Extracts from CHO cells expressing human AGT (lanes 1, 2) or its mutants P140A (lanes 3, 4) and G156A (lanes 5, 6) and extracts from HT29 cells (lanes 7, 8) were resolved by SDS-PAGE, transferred to nitrocellulose and developed using antibodies to a peptide corresponding to amino acids 8–20 of the human AGT. Untransfected CHO cells (lane 9) showed no AGT protein of this size. (Lanes 1, 3, 5—25 μg of protein loaded; lanes 2, 4, 6, 7—50 μg; lanes 8, 9—100 μg).

FIG. 2 shows the effect of different concentrations of BCNU on killing of CHO cells. Control CHO cells (▲) and CHO cells expressing human AGT (○) or its mutants P140A (●) and G156A (□) were treated with BCNU at the concentration shown for 2 h. The medium was then replaced. After 16–18 h, the cells were replated as described in Example Section 6 and colonies were counted 7–8 days later.

FIG. 3a and FIG. 3b show a loss of AGT activity after exposure to different concentrations of BG (FIG. 3a) and 5-nitroso-BP (FIG. 3b). CHO cells expressing human AGT (○) and its mutants P140A (●) and G156A (□) were exposed to BG or 5-nitroso-BP for 4 h. The cells were then harvested and the AGT activity determined.

FIG. 4 show the effect of BG on cell growth. Cells of a CHO clone expressing G156A AGT were seeded at $10^5$ per 75 cm$^2$ flask. After 48 h the medium was replaced with fresh medium containing different concentrations of BG as shown. The cells were maintained in the presence of BG for 24 h. After this time, the medium was replaced every 24 h. Cells were harvested and counted at time points indicated.

FIG. 5 show the effect of different concentrations of BG and 5-nitroso-BP on colony formation. BG was added to CHO cells expressing mutant AGTs P140 (●) and G156A (□) and 5-nitroso-BP was added to cells expressing G156A (■) for 18–20 h. The cells were then replated as described in materials and methods and colonies were counted 7–8 days later.

FIG. 6a and FIG. 6b show the effect of different concentrations of BG (FIG. 6a) and 5-nitroso-BP (FIG. 6b) on killing of cells by BCNU. Cells were treated with BG or 5-nitroso-BP at the concentrations indicated for 2 h and BCNU at 80 μM was added for 2 h. Medium was replaced with fresh medium also containing the AGT inhibitor but not BCNU for the period of 18 h. The cells were then replated as described in materials and methods and colonies were counted 7–8 days later.

5. DETAILED DESCRIPTION OF THE INVENTION

Figure 1:
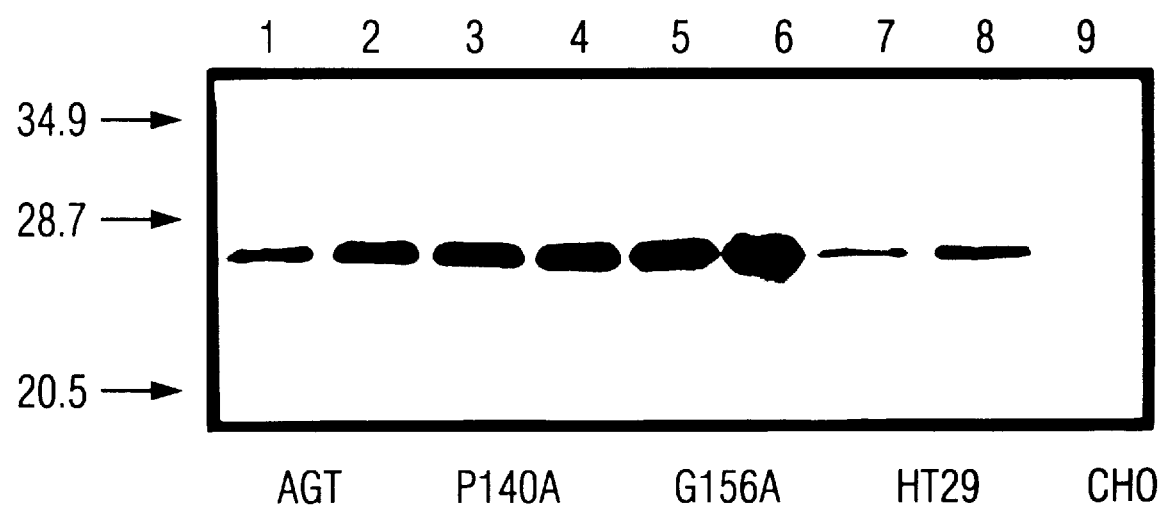

The present invention overcomes a major limitation in the use of alkylating and methylating agents in the treatment of neoplastic disease by addressing the problem of extreme myelosuppression produced by these drugs. The present invention overcomes this limitation by providing for methods of treating neoplastic disease whereby gene therapy methodology is combined with known chemotherapeutic regimes to optimize host tumor responsiveness to the anti-neoplastic agents administered to the patient.

The basis of the present invention is grounded in using gene therapy techniques in conjunction with chemotherapy regimes. This combination provides for a host environment whereby tumor cells are optimally sensitized to anti-neoplastic agents while transduced myeloid cells remain substantially unaffected.

There is a preferred scenario whereby the methods of the present invention will be particularly useful. It will be advantageous in certain cancer treatments to inactivate a specific tumor cell protein which is also expressed in non-malignant cell types. This will be accomplished by adding a compound to the chemotherapy regime known to inhibit a particular function of the protein. It follows that inactivating this biological function in non-malignant cell types may be deleterious to successful treatment of the patient. Therefore, a mutant protein shown to possess substantially wild type activity as well as imparting resistance to the inhibiting compound will be subcloned into a recombinant vector, transduced into a population of non-malignant cell types, such as hematopoietic stem and progenitor cells, and introduced back into the patient. The end result will be expression of the sensitive, wild type form of the protein in tumor cells as compared to a mutant version being expressed in hematopoietic cells. This mutant version will retain wild type function as well as being insensitive to the inhibitory compound. This combination of gene therapy and chemotherapy applications will provide maximum sensitivity of the tumor cells to anti-neoplastic agents while substantially decreasing myelosuppression within the patient.

Example Section 7 exemplifies targeting of hematopoietic cells, namely CD34$^+$ cells enriched from peripheral blood. Gene therapy based targeting of hematopoietic cells will be effective in overcoming myelosuppression associated with treatment of these anti-neoplastic drugs. However, this specification teaches the usefullness of targeting any non-malignant cell type, either by ex vivo or in vivo based methods, which will support biologically active concetrations of a human AGT mutant of the present invention.

To this end, a portion of the invention relates to use of gene therapy treatments to improve a chemotherapeutic regime wherein the tumor protein targeted for modification is O$^6$-alkylguanine-DNA alkyltransferase (AGT). It is known that the presence of AGT, a DNA repair protein active in mammalian tumor cells, imparts resistance to alkylating agents. The mechanism of action of AGT involves reaction with the O$^6$-position of guanine residues in DNA, the target for DNA adduct formation of many alkylating agents. It has been advantageous to inactivate tumor localized AGT so as to sensitize tumor cells to the alkylating agents. Tumor cells have been successfully sensitized by adding O$^6$-benzylated guanine derivatives, such as BG, to the chemotherapy regime (see Pegg, et al., 1995, Prog. Nucl. Acids 51: 167–223). These compounds have been shown to be effective inactivators of AGT and inclusion in a chemotherapy mix enhances cytotoxic properties of chloroethylating and methylating anti-tumor drugs (see, e.g. Chae, et al., 1994, J. Med. Chem. 35: 4486–4491). Regardless, addition of BG or a related O$^6$-benzylated guanine derivative does not address the problem of cytotoxicity within various host non-malignant cell types. In fact, inhibiting AGT in non-malignant cell types will exacerbate cytotoxicity in non-malignant cells expressing useful concentrations of AGT. An overriding problem of using alkylating agents in chemotherapy regimes has been severe myelosuppression caused by low levels of AGT expression. This problem will persist with or without addition of O$^6$-benzylated guanine derivatives.

Therefore, an embodiment of the present invention relates to the use of a mutant AGT protein, preferably a human AGT protein, resistant to inactivation by a compound shown to inactivate or at least substantially to inactivate the DNA repair function of wild type AGT. By way of example, and certainly not of limitation, compounds which may be utilized are O$^6$-benzylated guanine derivatives such as 8-aza-O$^6$-benzylguanine (8-aza-BG); O$^6$-benzyl-8-bromoguanine (8-bromo-BG); 2-amino-4-benzyloxy-5-nitropyrimidine (4-desamino-5-nitro-BP); O$^6$-benzylguanine (BG); O$^6$-[p-(hydroxymethyl)benzyl]guanine (HN-BG); O$^6$-benzyl-8-methylguanine (8-methyl-BG); O$^6$-benzyl-7,8-dihydro-8-oxoguanine (8-oxo-BG); 2,4,5,-triamino-6-benzyloxyprimidine (5-amino-BP); O$^6$-benzyl-9-[(3-oxo-5α-androstan-17β-yloxycarbonyl)methyl]guanine (DHT-BG); O$^6$-benzyl-9-[(3-oxo-4-androsten-17β-yloxycarbonyl)methyl]guanine (AND-BG); and, 8-amino-O$^6$-benzylguanine (8-amino-BG). In addition, pyrimidine compounds, including but not limited to 2,4-diamino-6benzyloxy-5-nitrosopyrimidine (5-nitroso-BP) and 2,4- diamino-6-benzyloxy-5-nitropyrimidine (5-nitro-BP) may be utilized in conjunction with a preferred AGT mutant.

Another embodiment of the present invention relates to the use of a mutant AGT protein, preferably a human AGT protein, resistant to inactivation by a compound shown to inactivate or at least substantially inactivate the DNA repair function of wild type AGT which include, but again are in no way limited to the $O^6$-substituted guanosine and 2' deoxyguanisine compounds disclosed in U.S. Pat. No. 5,352,669 issued to Moschel, et al. on Oct. 4, 1994. In an in vitro screen of potential AGT-inhibiting BG analogs, dBG, the 2'-deoxiribonucleoside was found to be 10-fold less potent than BG and BGs modified at the benzyl ring, but it was among the most active of the relatively soluble AGT inhibitors. The relatively high potency of dBG combined with its superior solubility in aqueous media compared to other BGs prompted us to test in an in vivo xenograft system. Despite a difference in in vitro potency between BG and dBG, the BCNU-potentiating effects of the two compounds were quite comparable. Furthermore, escalation of the dBG dose was not restricted by solubility as with BG. Therefore, this class of compounds, as exemplified by dBG, will be useful in practicing the present invention whereby the skilled artisan identifies a related AGT mutant which imparts resistance to addition of dBG both in vitro and in vivo.

Example Section 6 and Example Section 7 exemplify the use of human AGT sequence mutated at aa#140 (proline to alanine) and #156 (glycine to alanine). However, the skilled artisan will be fully aware that any mutation, whether it be a substitution mutant, deletion mutant or addition mutant, will be useful in the present invention as long as any such mutant shows resistance to the compound which inhibits wild type AGT and also retains DNA repair activity. It will be within the purview of an artisan of ordinary skill to generate additional mutants, and test such mutants with the aid of this specification, for use in practicing the disclosed invention. The combined use of such a mutant in gene therapy/chemotherapy applications will allow practically unfettered use of the compound of interest in chemotherapy regimes to sensitize target tumor cells while imparting both resistance and wild type AGT activity to the transduced hematopoietic cells and subsequent hematopoietic cells introduced back to the patient.

Therefore, in a specific example hematotoxicity will be overcome by use of gene therapy to express and alkyltransferase gene in the hematopoietic cells and/or hematopoietic stem or progenitor cells. A mutant human AGT resistant to inactivation by $O^6$-benzylated guanine derivatives and pyrimidine compounds, for example, will have considerable advantages for this purpose. The expression from a strong promoter of the resistant form of AGT in the patient's marrow will improve the therapeutic index of the treatment both by increasing the alkyltransferase activity in the critical hematopoietic cells and in rendering this AGT insensitive to inactivation by the modifying agent whereas the tumor AGT would still be sensitive to the respective compound.

It follows that another aspect of the present invention relates to utilizing the resistance of cells expressing a mutant AGT, as exemplified in Example Section 6, to select a population of hematopoietic progenitor cells expressing high levels of a stable AGT mutant for use in the disclosed gene therapy protocols. This selection procedure will be based on selecting cultured cells expressing high levels of at least one mutant form of AGT in the presence of (1) the compound or compounds which inhibit wild type activity but are inactive against the mutant, and (2) the alkylating agent of choice which will be at least one of the agents used in the planned chemotherapeutic regime.

It may be incumbent upon the skilled artisan to generate and test an AGT mutant resistant to a particular compound. As noted above, any such additional mutant is within the scope of the present invention and may be tested in conjunction with the data presented in Example Section 6. Although a mutant AGT resistant to a compound such as an $O^6$-benzylated guanine derivatives or a pyrimidine compound may show no apparent defect in the ability to repair an $O^6$-methylguanine in DNA in vitro, the rate of repair of methylated DNA is very rapid and is difficult to measure accurately under physiological conditions. It may not be evident as to whether the ability to act on the larger 2-chloroethyl group is affected by the respective mutation. Furthermore, some point mutations in AGT have a pronounced destabilizing effect and may reduce the steady state level of the AGT protein (see, e.g. Crone, et al., 1994, *Cancer Res.* 54: 6221–6227; Ling-Ling, et al., 1992, *Carcinogenesis* 13: 837–843; Pieper, et al. 1994, *Carcinogenesis* 15: 1895–1902). Any or all of these factors could limit the ability of the respective mutant AGTs to protect cells from chloroethylation. It is possible that any such mutation derived by in vitro means will not affect the ability to repair $O^6$-(2-chloroethyl)guanine in cellular DNA and would therefore not produce resistance to sensitization by a $O^6$-benzylated guanine derivative or a pyrimidine compound. Therefore, the assays exemplified in Example Section 5 will be necessary to predict the fidelity of a mutant for future transduction into hematopoietic progenitor and stem cells and reintroduction into the patient.

The present invention relates to the use of any available alkylating agent, such as chloroethylating agents, or other known compounds which may form one or more types of DNA adducts from which may be reversed by wild type AGT or a respective mutant AGT protein which substantially retains the wild type DNA repair function. In other words, the present invention contemplates the use, alone or in any combination recognized by the skilled practitioner, of one or more alkylating agents which alkylated DNA at the $O^6$-position in guanine. Examples of such alkylating agents, provided for the purpose of example and by no means of limitation, are the chloronitrosoureas N,N'-bis(2-cholorethyl)-N-nitrosourea (BCNU) and N-(2-cholorethyl)-3-cyclohexyl-N-nitrosourea (CCNU). These compounds may be utilized in combination with any exemplified or disclosed inhibitor of AGT and with any exemplified or disclosed transgene in a combination so as to sensitize tumor cells to the these alkylating agents while rendering transduced cells resistant to the inhibitor.

The present invention relates to the use of any available methylating agent or other similar compound which may form one or more types of DNA adducts from which may be reversed by wild type AGT or a respective mutant AGT protein which substantially retains the wild type DNA repair function. As noted in the previous paragraph for use of alkylating agents, the present invention contemplates the use, alone or in any combination recognized by the skilled practitioner, of one or more methylating agents which form a DNA adduct at the $O^6$-position in guanine. Examples of such methylating agents, provided for the purpose of example and by no means of limitation, are temozolomide, decarbazine, procarbazine, and streptozotocin. These compounds may be utilized in combination with any exemplified or disclosed inhibitor of AGT and with any exemplified or disclosed transgene in a combination so as to sensitize tumor cells to the alkylating agents while rendering transduced cells resistant to the inhibitor.

The $O^6$-benzylguanine derivatives employed in the present invention may be made into pharmaceutical compositions by accommodation with appropriate pharmaceutically acceptable excipients or carriers or diluents, and may be formulated into preparations in solid, semi-solid, liquid or gaseous forms such as tablets, capsules, powders, granules, ointments, solutions, suppositories, injections, inhalants, and aerosols in the usual ways for their respective route of administration. The following methods and excipients are merely exemplary and are in no way limiting.

In pharmaceutical dosage forms, the $O^6$-benzylguanine derivatives employed in the present invention may be used in the form of their pharmaceutically acceptable salts, and also may be used alone or in appropriate association, as well as in combination with other pharmaceutically active compounds.

In the case of oral preparations, the $O^6$-benzylguanine derivatives of the present invention may be used alone or in combination with appropriate additives to make tablets, powders, granules or capsules, e.g. with the conventional additives such as lactose, mannitol, corn starch or potato starch; with binders such as crystalline cellulose, cellulose derivatives, acacia, corn starch or gelatins; with disintegrators such as corn starch, potato starch or sodium carboxymethylcellulose; with lubricants such as talc or magnesium stearate; and, if desired, with diluents, buffering agents, moistening agents, preservatives and flavoring agents.

Furthermore, the $O^6$-benzylguanine derivatives employed in the present invention may be made into suppositories by mixing with a variety of bases such as emulsifying bases or water-soluble bases.

The $O^6$-benzylguanine derivatives employed in the present invention may be formulated into preparations for injections by dissolving, suspending or emulsifying them in an aqueous or non-aqueous solvent, such as vegetable oil, synthetic aliphatic acid glycerides, esters of higher aliphatic acids or propylene glycol; and if desired, with conventional additives such as solubilizers, isotonic agents, suspending agents, emulsifying agents, stabilizers and preservatives.

In the cases of inhalations or aerosol preparations, the $O^6$-benzylguanine derivatives employed in the present invention in the form of a liquid or minute powder may be filled up in an aerosol container with gas or liquid spraying agents, and if desired, together with conventional adjuvants such as humidifying agents. They may also be formulated as pharmaceutical for non-pressured preparations such as via a nebulizer or an atomizer.

The amount of $O^6$-benzylguanine derivatives employed in the present invention to be used varies according to the degree of the effective amount required for treating tumor cells. A suitable dosage is that which will result in a concentration of the $O^6$-benzylguanine derivatives in the tumor cells to be treated which results in the depletion of AGT activity, e.g. about 1–2000 mg/kg prior to chemotherapy and preferably 10–800 mg/kg prior to chemotherapy. In fact, a basis for the present invention is the use of gene therapy applications in conjunction with the addition of BG such that higher doses of BG may be added without the documented deleterious effects on non-malignant cell types.

Unit dosage forms for oral administration such as syrups, elixirs, and suspensions wherein each dosage unit (e.g. teaspoonful or tablespoonful) contains a predetermined amount of the $O^6$-benzylguanine derivative employed in the present invention can be combined with a pharmaceutically acceptable carrier, such as Sterile Water for Injection, USP, or by normal saline.

The $O^6$-benzylguanine derivatives employed in the present invention can be administered rectally via a suppository. The suppository can include vehicles such as cocoa butter, carbowaxes and polyethylene glycols, which melt at body temperature, yet are solidified at room temperature.

The $O^6$-benzylguanine derivatives employed in the present invention can be administered transdermally in an appropriate vehicle or salt or converted to a salt. Adsorption may be aided by the use of an electric current or field.

The $O^6$-benzylguanine derivatives employed in the present invention may be administered with an appropriate vehicle for buccal or sublingual administration.

The $O^6$-benzylguanine derivatives employed in the present invention can be utilized in aerosol formulations to be administered via inhalation. The $O^6$-benzylguanine derivatives can be formulated into pressurized acceptable propellants such as dichlorodifluoromethane, propane, nitrogen and the like.

The term "unit dosage form" as used herein generally refers to physically discrete units suitable as unitary dosages for human and animal subjects, each unit containing a predetermined quantity of the $O^6$-benzylguanine derivatives calculated in an amount sufficient to produce the desired effect in association with a pharmaceutically acceptable diluent, carrier, excipient or vehicle. The specifications for the novel unit dosage forms of the present invention depend on the particular compound employed and the effect to be achieved, and the pharmacodynamics associated with each compound in the host.

The pharmaceutically acceptable excipients, for example, vehicles, adjuvants, carriers or diluents are readily available to the public.

Any necessary adjustments in dose can be readily made to meet the chemotherapeutic treatment requirements and adjusted accordingly by the skilled practitioner.

A preferred mode of BG delivery is via a PEG 400/saline solution. This delivery vehicle has been studied in detail, is practically non-toxic, has been given to humans orally and is present in commercial drug formulations such as lorazepam for injection. The use of a PEG 400 saline solution has been shown to be an appropriate vehicle for delivery of BG (Dolan, et al., 1994, *Cancer Chemother. Pharmacol.* 35: 121–126).

This specification teaches combinational gene/chemotherapy. Combinations of dosage and timing and intervals introduction of transduced cells to optimize treatment of patient will be required and are within the scope of the present invention.

These compounds may be administered using conventional techniques such as those described in Wasserman, et al., 1975, *Cancer* 36: 1258–1268; and Physician's Desk Reference, $45^{th}$ ed., 1991, Edward R. Barnhart (publisher). For example, BCNU may be administered intravenously at a dosage from about 150–200 mg/m$^2$ every six weeks. CCNU may be administered orally at a dosage of about 130 mg/m$^2$ every six weeks. Other additional alkylating or methylating agents may be administered in appropriate dosages via appropriate routes of administration known to the skilled artisan.

A specific embodiment of the present invention relates to using a mutated nucleic acid sequence which expresses an AGT protein, preferably a human protein, which is resistant to BG while still retaining wild type or near wild type ability to repair DNA adducts formed after exposure to various chloroethylating agents. The transduction and expression of such an AGT mutant gene in hematopoietic cells followed by reintroduction of the transduced cells into the mammalian host will result in an in vivo cell population which both shows an elevated level of the mutant AGT and in turn is not sensitive to the presence of BG as a chemotherapeutic agent. In vivo expression of a BG-resistant AGT mutant protein will, as disclosed above, overcome the effect of a chloroethylating agent not only through elevated concentrations of the protein but also due to resistance to BG.

In a specific embodiment of the present invention gene therapy treatments disclosed within this specification are utilized in tandem with a chemotherapeutic regime comprising BG and the chloroethylating agent N,N'-bis(2-cholorethyl)-N-nitrosourea (BCNU).

It will be advantageous to select an AGT mutant exhibiting both optimal resistance to the $O^6$-benzylated guanine derivatives or a pyrimidine compound of choice as well as retaining wild type or substantially wild type function. This selection can occur not only in cultured CHO cells as shown in Example Section 6 but will also continue during infection of hematopoietic cells. It will be advantageous and is forwarded as a portion of the present invention to select recombinant AGT retroviral clones expressing high levels of the mutant AGT of interest. This may be accomplished by selecting for positive clones during the initial co-culture with producer cells in the presence of an alkylating agent and/or the $O^6$-benzylated guanine derivatives or a pyrimidine compound of choice. Additionally or in combination with the latter, selection may occur during co-culture of the retroviral supernatant with hematopoietic cells. Only recombinant retroviral AGT mutants expressed at adequate levels will impart resistance in culture to the $O^6$-benzylated guanine derivatives or a pyrimidine compound while exhibiting wild type activity. It will be a recombinant AGT retroviral vector with such characteristics which will lead to a greater therapeutic index when reintroduced into the patient in conjunction with anti-neoplastic alkylating or methylating agents.

The present invention also relates to methods of in vitro screening and selection of additional compounds which will inhibit wild type AGT while imparting no effect on DNA repair activity of a known, functional AGT mutant.

The present invention also relates to methods of in vitro screening and selection of additional AGT mutants which retain substantial amounts of wild type DNA repair activity while imparting resistance to a particular compound or compounds known to inhibit wild type AGT activity.

It is contemplated in the present invention that a transgenic construct of interest be delivered to hematopoietic cells by viral-mediated means. Recombinant virus vectors utilized in the present invention include, but are not limited to (a) retroviral vectors, including but not limited to vectors derived from a Moloney murine leukemia virus (MoMLV) or a myeloproliferative sarcoma virus (MPSV); (b) adenovirus vectors; (c) adeno-associated vectors; (d) herpes simplex virus vectors; (e) SV40 vectors; (f) polyoma virus vectors; (g) papilloma virus vectors; (h) picornavirus vectors; and, (i) vaccinia virus vectors. Depending on the virus vector system chosen, techniques available to the skilled artisan are utilized to infect the target cell of choice with the recombinant virus vector.

In a specific embodiment of the present invention a transgenic construct of interest is subcloned into the retroviral vector MFG. This recombinant MFG retroviral vector is transferred into a packaging cell line and the recovered viral particles are used to transfect a mammalian cell population line, including but not limited to (1) peripheral blood mononuclear cell populations, preferably enriched for $CD34^+$ progenitors, and (2) bone marrow cell populations containing hematopoietic progenitor cells, preferably enriched for $CD34^+$ progenitors. The in vitro transfected cell populations are then reintroduced into the patient by known techniques.

A specific embodiment of the invention regarding optimization of a chemotherapy regime including a chloroethylating agent in tandem with BG involves use of the human AGT mutant P140A, wherein proline #140 has been substituted with alanine.

Another specific embodiment of the invention regarding optimization of a chemotherapy regime including a chloroethylating agent in tandem with BG involves use of the human AGT mutant G156A, wherein glycine #156 has been substituted with alanine.

In another embodiment of the invention the human AGT mutant P140A may be subcloned in a MFG retroviral vector, thus generating a MFG-hAGT/P140A recombinant retroviral vector for transduction into hematopoietic cells and reintroduction into the patient as part of the chemotherapeutic regime comprising at least a compound to which P140A AGT shows resistance as well as an alkylating or methylating agent used in the treatment of a neoplastic disease.

In a preferred embodiment of the invention the human AGT mutant P140A may be subcloned in a MFG retroviral vector, thus generating a MFG-hAGT/P140A recombinant retroviral vector for transduction into hematopoietic cells and reintroduction into the patient as part of the chemotherapeutic regime utilized in tandem with a chemotherapeutic regime comprising BG and the chloroethylating agent N,N'-bis(2-cholorethyl)-N-nitrosourea (BCNU).

In a preferred embodiment of the invention the human AGT mutant G156A may be subcloned in a MFG retroviral vector, thus generating a MFG-hAGT/G156A-based recombinant vector which is exemplified in Example Section 7 and referred to throughout this specification simply as MFG-ΔMGMT. This recombinant retroviral vector is then transduced into hematopoietic cells where selected transduced cells are reintroduced into the patient as part of the chemotherapeutic regime comprising at least a compound which G156A AGT shows resistance as well as an alkylating or methylating agent used in the treatment of a neoplastic disease.

In an especially preferred embodiment of the invention the human AGT mutant G156A may be subcloned in a MFG retroviral vector, thus generating MFG-ΔMGMT for transduction into hematopoietic cells and reintroduction into the patient as part of the chemotherapeutic regime utilized in tandem with a chemotherapeutic regime comprising BG and the chloroethylating agent N,N'-bis(2-cholorethyl)-N-nitrosourea (BCNU). Again, this MFG-hAGT/G156A based recombinant retroviral vector is exemplified in Example Section 7 and is referred to throughout this specification as MFG-ΔMGMT.

The present invention also includes methods of dominant selection of a second transduced gene in hematopoietic cells wherein a first transduced gene expressing an AGT mutant resistant to an $O^6$-benzylated guanine derivative is co-cultured in the presence of the $O^6$-benzylated guanine derivative and an alkylating or methylating agent. A marked enhancement of clonogenic survival of $CD34^+$ cells transduced with the transgene expressing G156A AGT in the presence of BG and BCNU shows that any AGT mutant showing similar activity will be useful as a drug resistance gene.

6. EXAMPLE: IN VITRO EXPRESSION AND BIOLOGICAL ACTIVITY OF HUMAN AGT MUTANTS

6.1 MATERIALS AND METHODS

Materials—BG and 5-nitroso-BP were synthesized and supplied by Dr. R. C. Moschel (NCI-FCRDC, Frederick, Md.). BCNU was obtained from the Drug Synthesis and Chemistry Branch, Division of Cancer Treatment, NCI, Bethesda, Md. N-[$^3$H]methyl-N-nitrosourea was purchased from Amersham Inc., Arlington Hts., Ill. Other reagents for molecular biology, cell culture and AGT assays were obtained from: GIBCO BRL Life Technologies, Gaithersburg, Md.; Sigma, St Louis, Mo.; Atlanta Biologicals, Norcross, Ga.; New England Biolabs, Beverly, Mass.; Perkin Elmer, Branchburg, N.J.; and Promega, Madison, Wis.

Plasmid Constructions—In order to express AGT in Chinese hamster ovary (CHO) cells, the plasmid pCMV-Neo-Bam (Baker, et al., 1990, *Science* 249: 912–915) which has a CMV promoter controlling the expression of the sequences inserted at a unique BamHI site and a neomycin resistance gene for selection by geneticin of clones which have taken up the plasmid. The cDNAs corresponding to wild type, P140A and G156A AGTs were obtained by PCR using pGEMAGTs containing these inserts (Crone and Pegg, 1993, *Cancer Res.* 53: 4750–4753; Crone, et al., 1994, *Cancer Res.* 54: 6221–6227, hereby incorporated by reference). The primer used for the 3' end corresponded to the SP6 RNA polymerase promoter sequence and the primer for the 5' end was 5'-CTCACTATAGG<u>A</u>TCCA<u>AAA</u>TGGACAAGGAT-3'(SEQ ID NO:1) (mismatches underlined). This primer creates a BamHI restriction site and also restores the initiation codon of the AGT sequence. The PCR product was digested with BamHI and inserted into pCMV-Neo-Bam at the BamHI site. Plasmids were isolated and checked for the insertion of the AGT sequence in the correct direction by digestion with XbaI and DraIII which cut unique sites in the vector and the AGT cDNA respectively. The AGT sequence in a plasmid showing the correct orientation was then verified by sequencing.

Cell culture—CHO cells were maintained by seeding at $2.5 \times 10^6$ cells per 75 cm$^2$ flask and grown in α-MEM medium containing 36 mM NaHCO$_3$, 10% fetal calf serum, 100 units/ml penicillin and 100 μg/ml streptomycin. HT29 cells were grown in Dulbecco's modified Eagle's medium containing 36 mM NaHCO$_3$ supplemented with 10% fetal calf serum plus 3% glutamine and gentamycin (50 μg/ml).

Transfection and selection procedure—CHO cells were transfected using Lipofectin (GIBCO BRL) according to manufacture's protocol for stable transfection of adherent cells. Cells were seeded at 10$^5$ cells in 60 mm tissue culture plates. For each transfection, 2 μg DNA and 10 μl Lipofectin diluted in serum-free antibiotic-free medium were used. Cells were incubated for 5 h then the DNA containing medium was replaced with growth medium. At 48 h later, geneticin (GIBCO BRL) was added at a final concentration of 1 mg/ml to select the cells expressing the neomycin resistance gene. In addition, the cells transfected with AGT and mutant P140A AGT were selected for their resistance to killing effect of BCNU (80 μM). Clones from individual cell colonies were isolated and used for further experiments.

Cell growth—In order to determine the effect of BG on the rate of cell growth, the cells were seeded at 10$^5$ cells per 75 cm$^2$ flask and allowed to grow for 48 h. The medium was then replaced with fresh medium or fresh medium containing different concentrations of the drug. After 24 h, the medium was replaced and cells were allowed to grow fill they reach 90% of confluence in a control flask. The medium was changed every 24 h. Control cells and cells after exposure to BG were harvested and counted at different time points.

Cytotoxicity assays—Cell killing was determined using a colony forming assay (Pegg, et al., 1995, *Biochem. Pharmacol.* 50: 1141–1148; Dolan, et al., 1986, *Cancer Res.* 46: 4500–4504). The cells were plated using 10$^6$ cells per 25 cm$^2$ flask and grown for 24 h. After 2 h of incubation with either BG or 5-nitroso-BP, 80 μM BCNU was added for 2 h. The medium was then replaced with fresh medium also containing the AGT inactivator and the cells were left at 37° C. for an additional 16–18 h. The cells were then replated at densities of 100 to 1000 cells per 25 cm$^2$ flask and grown for 7–8 days until discrete colonies could be stained and counted. The colonies were washed with 0.9% saline and stained with crystal violet and counted.

AGT activity assays—Extracts were prepared and AGT activity was determined as described by Dolan et al. (Dolan, et al., 1990, *Proc. Natl. Acad. Sci. U.S.A.* 87: 5368–5372) by incubation for 30 min at 37° C. with a [$^3$H]methylated calf thymus DNA substrate prepared by reaction of DNA with N-[$^3$H]methyl-N-nitrosourea (Amersham Inc., Arlington Hts., Ill.). The AGT activity of the cells was then expressed as fmol of O$^6$-methylguanine removed per mg of protein present in the cell extracts. Protein was determined by the method of Bradford (Bradford, 1976, *Anal. Biochem.* 72: 248–254). Inactivation of cellular AGT was measured by adding different concentrations of BG or 5-nitroso-BP to cell cultures which had reached about 80% confluence. After 4 h exposure, the cells were harvested and washed with PBS. Cell pellets were stored at −80° C. until assayed. Extracts were then prepared and AGT activity determined. The results were expressed as the percentage of the AGT activity present in cultures to which no drug was added.

Western blot analysis—The expression of the wild type and mutant AGT proteins in transfected CHO cells was measured using immunoblots. After SDS-PAGE in 12.5% acrylamide gels, the protein immobilized on the nitrocellulose membrane was determined by Western-Light Chemiluminescent Detection System (TROPIX, Inc.) using antibody MAP-1 (Pegg, et al., 1991, *Carcinogenesis* 12: 1671–1677). The intensity of chemiluminescence was measured by densitometric scanning using a laser densitometer.

6.2. RESULTS

AGT activity was measured in individual clones of CHO cells after their transfection with the pCMV plasmids expressing human cDNA for wild type and mutant AGTs. The activity in untransfected CHO cells was below the limit of detection but multiple clones expressing high levels of AGT were readily obtained from the pools of transfected cells. There was a considerable range in AGT activities among the various clones. Those clones selected on the basis of resistance to BCNU as well as to G418 had on average a higher AGT activity but the range of activities observed in the two groups overlapped. Three clones containing equivalent activities of wild type, P140A and G156A mutant AGT were taken and used for further experiments. As shown in Table 1, these clones had AGT activities which were very similar and were about 2.5 times greater than that of HT29 cells. AGT protein could readily be measured in extracts from these cells using immunoblots developed with an antibody to a peptide corresponding to amino acids 8–20 of the human AGT sequence (FIG. 1). A single protein was detected with a M. W. of about 22 kDa. This band was completely absent from the untransfected CHO cells. Compared to the HT29 cells there was about 5.5 times more protein reacting with antibodies in the CHO cells transfected with wild type AGT, 8.2 times more for those with P140A and 11.5 times more in case of G156A according to densitometric measurement of these Western blots. These results suggest that some of the AGT in the transfected cells is inactive and that a larger fraction of the mutant AGT is non-functional since the measured AGT activities were the same and only 2.5 times more than the HT29 cells.

TABLE 1

Activity of AGT in transfected CHO cells and its inactivation by BG and 5-nitroso-BP

| Cells | AGT activity (fmol/mg) | Inactivation of AGT by BG or 5-nitroso-BP, $ED_{50}$ ($\mu M$) after 4 h exposure | |
|---|---|---|---|
| | | BG | 5-nitroso-BP |
| HT29 | 456 | 0.05[a] | 0.02[b] |
| CHO-AGT | 1144 | 0.5 | 0.05 |
| CHO-P140A | 1082 | 15 | 1.25 |
| CHO-G156A | 1152 | 30 | 5 |

[a]Dolan, et al., 1990, Proc. Natl. Acad. Sci. U.S.A. 87: 5368–5372.
[b]Pegg, et al., 1995, Biochem. Pharmacol. 50: 1141–1148.

Figure 2:
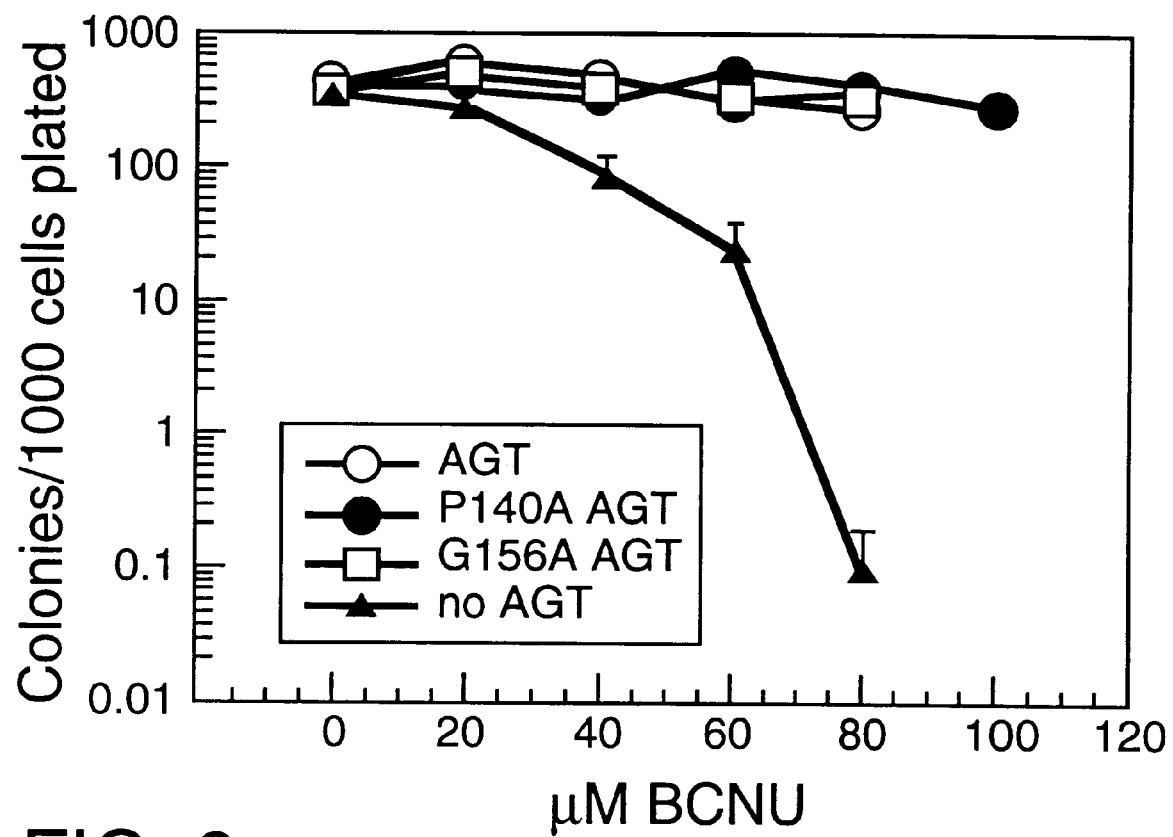

Control CHO cells were effectively killed by BCNU with less than 0.1% survival after 80 $\mu M$ BCNU. In contrast, the transfected cells expressing control or mutant AGT were completely resistant to killing by up to 100 $\mu M$ BCNU which was the highest concentration tested (FIG. 2).

Figure 3A:
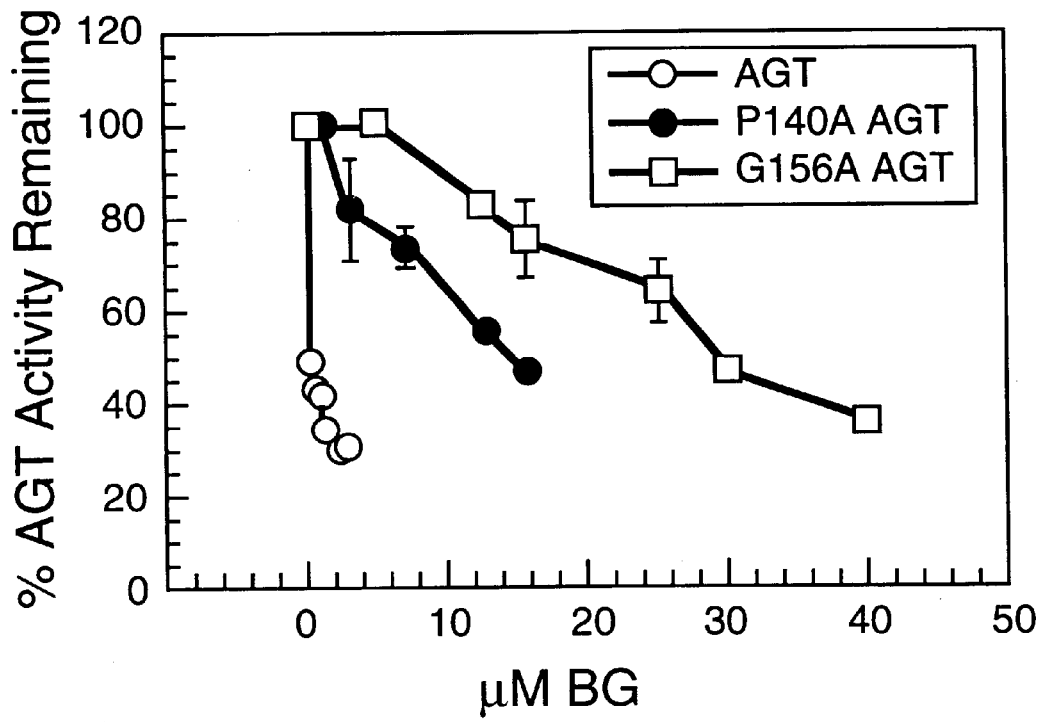
Figure 3B:
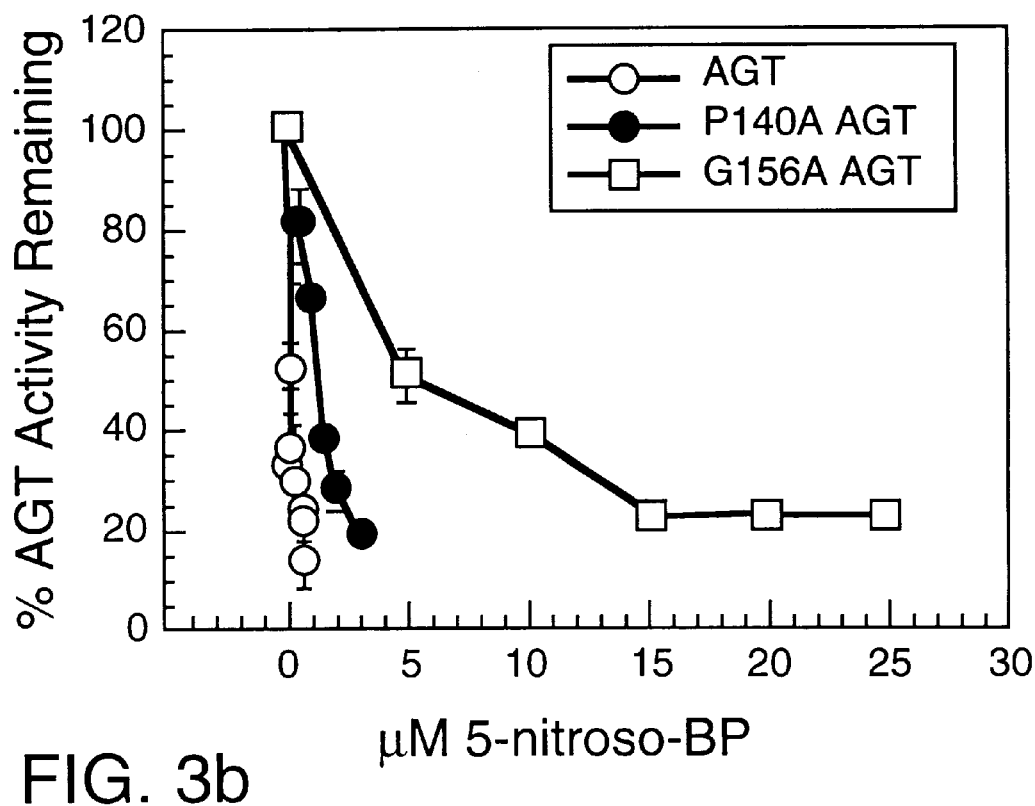

The AGT activity in the cells expressing control AGT was readily decreased by exposure of the cells to BG or 5-nitroso-BG (FIGS. 3a, 3b). Considerably more of these drugs had to be used to obtain the same inhibition of AGT in the cells expressing P140A AGT and those expressing G156A were even more resistant. The 5-nitroso-BP was more active than BG as an AGT inactivator in all three cell lines (FIG. 3b). A summary of the inactivation based on the concentration of drug needed to reduce AGT activity by 50% in the 4 h exposure period [$ED_{50}$] is shown in Table 1. The $ED_{50}$ for BG was increased by 30-fold to 15 $\mu M$ with P140A AGT and by 60-fold to 30 $\mu M$ with G156A. Similarly, the $ED_{50}$ for 5-nitroso-BP was increased by 25-fold to 1.25 $\mu M$ with P140A AGT and by 100-fold to 5 $\mu M$ with G156A AGT.

Figure 4:
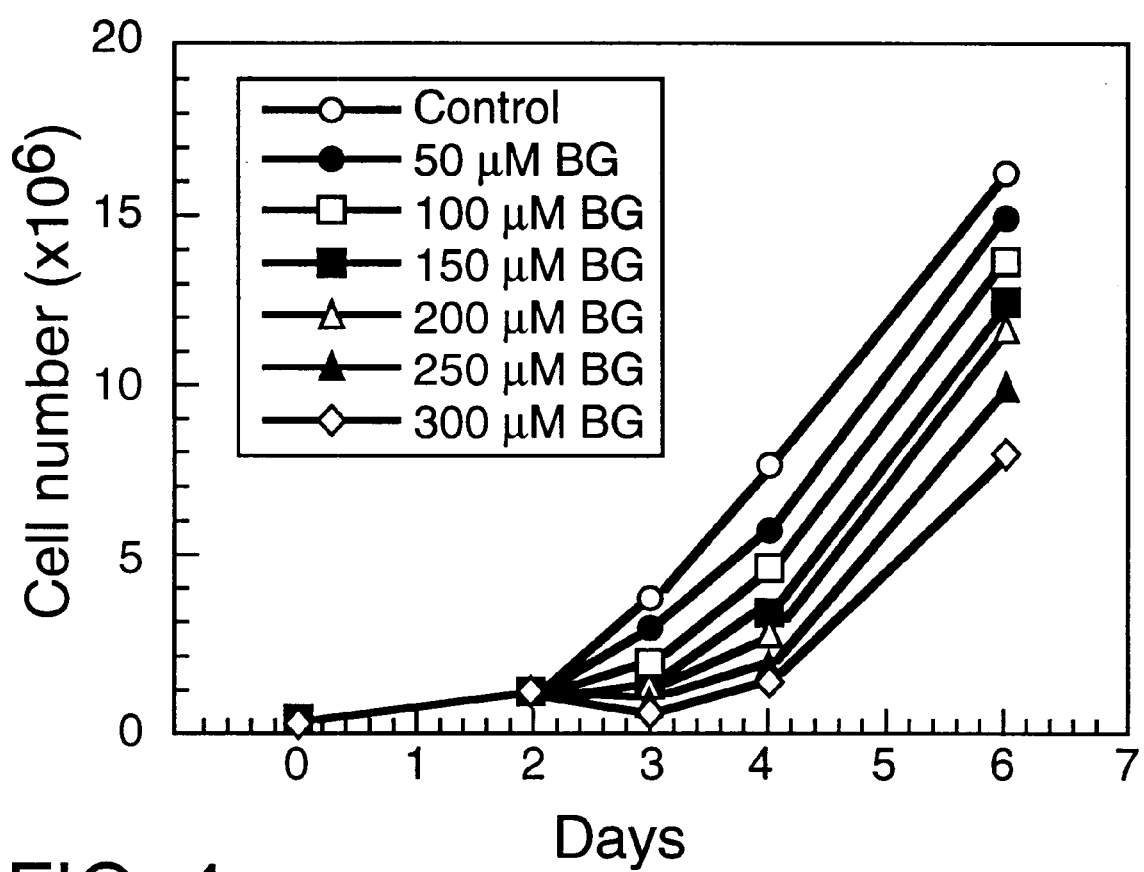
Figure 5:
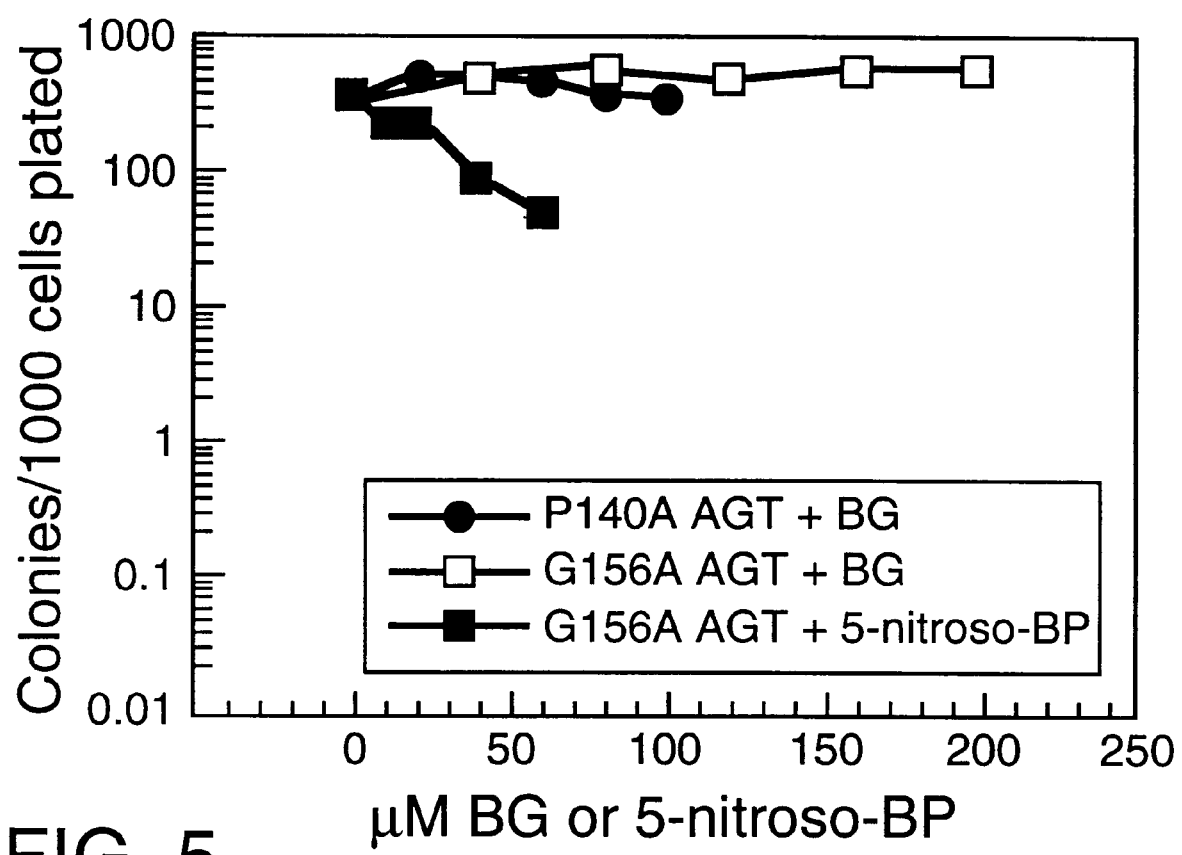

These results suggest that much higher levels of these AGT inhibitors may be needed to render the cells expressing mutant AGT sensitive to BCNU. Such high concentrations might have an effect on cell growth invalidating the colony forming assays so a control experiment was carried out to determine the effect of BG on cell growth. Exposure to BG for 24 h led to dose-dependent inhibition of cell growth with concentrations higher than 200 $\mu M$ having a profound effect on cell growth during the 24 h after the drug was removed from the medium (FIG. 4). However, during the next 48 h these cells recovered and were growing at the same rate as control cells. Since the effect of BG on cell growth was clearly reversible, the effects of exposure to the AGT inhibitors on colony forming ability could be determined (FIG. 5). Although the colonies observed were smaller in size (by a factor of up to 3 corresponding to a reduction of about 40% in the number of cells making up a colony) with the higher concentrations of BG due to the inhibition of growth in the first 24 h, the cells were grown for a further 7 days so that smaller colonies were detected as readily as larger ones. The results showed that exposure to BG for 20 h had no effect on colony forming activity up to 200 $\mu M$ BG. However, 5-nitroso-BP was more toxic with concentrations above 30 $\mu M$ reducing colony formation.

Figure 6A:
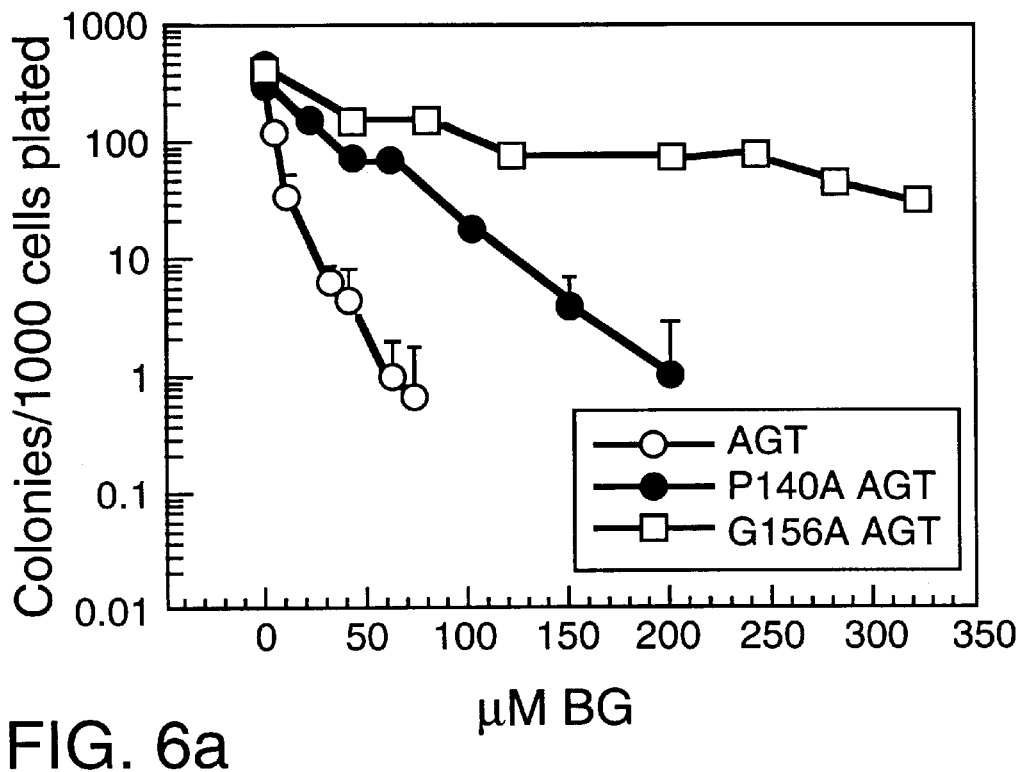

Addition of BG to CHO cells expressing control AGT rendered them highly sensitive to 80 $\mu M$ BCNU with 50 $\mu M$ BG being required to reduce colony formation to <1 per 1000 cells plated (FIG. 6a). This level of BG is considerably greater than that needed to sensitize a wide variety of human tumor cells to BCNU (see e.g., Pegg, et al., 1995, Progr. Nucleic Acid Res. Mol. Biol. 51: 167–223; Dolan, et al., 1990, Proc. Natl. Acad. Sci. U.S.A., 87: 5368–5372; Pegg, et al, 1995, Biochem. Phannacol. 50: 1141–1148; Dolan, et al., 1986, Cancer Res. 46: 4500–4504. This difference is probably due to the high level of AGT in the transfected CHO cells which was 2.5 times that of HT29 cells which are among the highest expressors of AGT in human cell lines. Another factor may be the fact that AGT in the CHO cells is expressed from the CMV promoter.

The CHO cells transfected with mutant AGT cDNAs were much more resistant to sensitization by BG (FIG. 6a). The addition of 200 $\mu M$ BG was needed to reduce colony formation in the BCNU treated cells to <1 per 1000 cells plated in the cells expressing P140A AGT. The cells expressing G156A AGT were even more refractory to the combined effects of BG and BCNU with substantial survival even in the presence of 350 $\mu M$ (FIG. 6a).

Figure 6B:
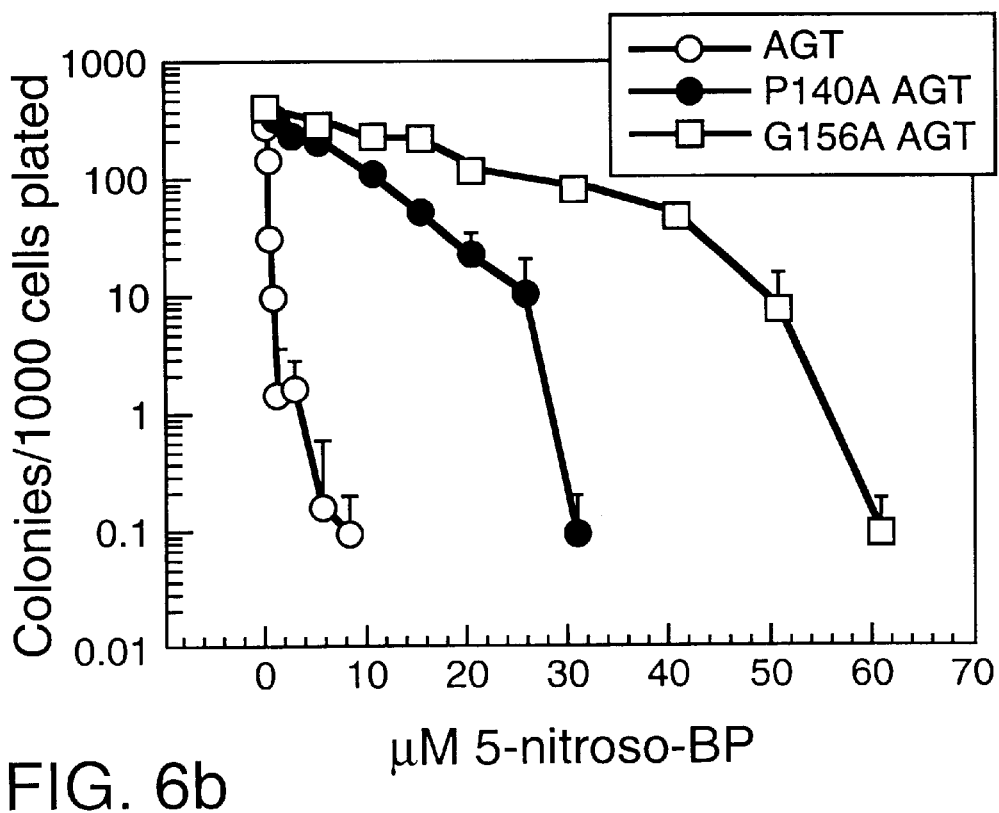

As shown in FIG. 6b, 5-nitroso-BP was very effective in sensitizing the CHO cells containing control AGT with about 5 $\mu M$ required for the reduction of colony formation to <1 per 1000 cells plated. More than 25 $\mu M$ of 5-nitroso-BP was needed to sensitize the cells expressing P140A AGT and cells expressing G156A mutant AGT required concentrations of >40 $\mu M$ which as shown in FIG. 5 affect colony formation even in the absence of BCNU.

These data presented in this example show clearly that the mutant P140A and G156A AGTs are sufficiently stable in the cell and active on the repair of chloroethyl groups in DNA to provide complete protection from killing by BCNU. Although these experiments were carried out in Chinese hamster cells, it is extremely likely that this conclusion would also be valid in both human tumor cells and in non-malignant cells. Our experiments to establish the ability of the mutant AGTs to provide protection were carried out in CHO cells for several reasons. First, the ease of transfection and cloning of these cells made it possible to obtain clones expressing similar levels of AGT activity for control and mutant AGT cDNAs. This is critical for accurate comparison of the effects of AGT expression on protection from BCNU. Second, the use of CHO cells allows us to be certain that the expressed AGT does come from the plasmid cDNA rather than from the activation of a hamster gene since the antibodies used react exclusively with the human protein (Pegg, et al., 1991, Carcinogenesis 12: 1679–1683). Such activation has been shown to have occurred in other studies (Pegg, et al., 1991, Carcinogenesis 12: 1679–1683; Tano, et al., 1991, Mutation Res. 255: 175–182; von Wronski and Brent, 1994, Carcinogenesis 15: 577–582; Arita, et al., 1990, Carcinogensis 11: 1733–1738). Third, other studies show that expression in CHO cells of human DNA proteins including AGT has been studied for its effects on cellular physiology. Thus, previous studies have shown that the expression of normal mammalian or bacterial AGTs in CHO renders the cells resistant to the toxic effects of alkylating agents. The results shown in this Example are similar to those found when AGT is expressed in human tumor cells or in transgenic mice (see review, e.g. Mitra and Kaina, 1993, Nucleic Acid Res. 44: 109–142; Pegg, A. E., 1990, Cancer Res. 50: 6119–6129; Pegg, et al., 1995, Nucleic Acid Res. Mol. Biol. 51: 167–223; Gerson, et al., 1994, Mutation Res. 307: 541–555).

Despite the differences in the content of protein revealed by Western blotting, no obvious differences in the stability of the mutant and control AGT proteins in the CHO cells were observed. The protein was too stable for measurement of its half life of decay after treatment with a protein synthesis inhibitor. Although the mammalian AGT proteins are highly conserved, it is more likely that a reduced stability (or incorrect folding) of the human AGTs protein would be observed in the foreign environment of a rodent cell than in the human cells. Therefore, it is highly probable that these mutant proteins will be sufficiently stable and active in both normal and neoplastic human cells to prevent lethal crosslinking by chloroethylating agents. The fate of the alkylated (or benzylated) form of the AGT protein produced by its reaction with alkylated DNA or BG respectively is still not well understood. In some cell lines, including both HT29 cells and CHO cells, this protein is degraded rapidly (Gerson, et al., 1994, *Mutation Res.* 307: 541–555) and recent studies with HT29 and CEM human tumor lines suggest that ubiquitination may be involved in this process (Pegg, et al., 1991, *Carcinogenesis* 12: 1679–1683). However, another study (Ayi, et al., 1994, *Cancer Res.* 54, 3726–3731) the alkylated form of the protein was reported to be sufficiently stable in CEM and HeLa S3 cells to be detected by Western blotting although a conformational change to increase cleavage by protease V8 was detected. Whether these results represent a significant difference in how the AGT protein is regulated in different cell types remains to be determined but, in any event, the CHO cells have similar properties to the human colon carcinoma HT29 cells with respect to the degradation of the alkylated AGT protein.

The results presented in FIGS. 3 and 6 show clearly that the point mutations at position $Pro^{140}$ and $Gly^{156}$ do render the human AGT resistant to BG and thereby reduce the ability of this drug to sensitize cells having such AGTs to BCNU. BG is currently entering clinical trials as a means to render tumor cells containing high levels of AGT sensitive to chloroethylating agents (Gerson, et al, 1994, *Proc. Am. Assn. Cancer Res.* 35: 699–700; Pegg, et al., 1995, *Progr. Nucleic Acid Res. Mol. Biol.* 51: 167–223). The selection of tumor cells expressing forms of AGT insensitive to this drug is a potentially serious problem since several single amino acid changes have been shown to impart such resistance. These data from this Example Section strengthen this concern since the results presented here show that at least two of these alterations (P140A and G156A) do lead to an AGT activity in cells which is able to protect from the toxicity of BCNU even in the presence of BG. Based on the solubility and pharmacokinetics of BG in animals (Dolan, et al., 1994, *Cancer Chemotherapy* 35: 121–126) and preliminary studies in primates (Berg, et al., 1995, *Cancer Res.* 55: 4606–4610), it is unlikely that plasma levels of BG of greater than 20 $\mu$m can readily be achieved. These levels are capable of completely inactivating the control AGT in a variety of human tumor cells (see, e.g. Gerson, et al., 1994, *Proc. Am. Assn. Cancer Res.* 35: 699–700; Pegg, et al., 1995, *Nucleic Acid Res. Mol. Biol.* 51: 167–223) and produce a large increase in killing by BCNU. In contrast, the levels of BG that are needed to produce sensitization of the transfected CHO cells when the P140A and G156A mutant AGTs were used are much greater than the predicted plasma levels.

This problem may be overcome by producing inhibitors that are active even against the resistant mutant forms of AGT. Such inhibitors fall into two classes: those which are able to inactivate the mutant forms as readily as they inactivate the control AGT; and those which are much more potent than BG so that a plasma level could be maintained that inactivates the mutant AGT proteins even though there is a difference in reactivity with the mutant compared to the control AGT. 5-nitroso-BP, which is the most potent AGT inhibitor so far reported on the basis of its ability to inactivate AGT in HT29 cells and cell extracts and to sensitize a variety of tumors to BCNU is not sufficiently active for this purpose.

It is very likely that a major reason for the resistance of the mutant forms of human AGT and the AGTs from microorganisms to BG is due to a steric limitation at the active site (see, e.g., Pegg, et al., 1995, *Progr. Nucleic Acid Res. Mol. Biol.* 51: 167–223; Pegg, et al., *Biochemistry* 32: 11998–12006). Although the structure of the AGT has not yet been determined, the mutations that render it resistant are in residues that may decrease the size of the active site pocket. Furthermore, alterations of the *E. coli* Ada-C alkyltransferase, which are predicted on the basis of the crystal structure to increase the accessibility of the cysteine acceptor site, do render it sensitive to BG (Crone, et al., 1995, *Carcinogenesis* 16: 1687–1692). As more information becomes available on the size of the active site pocket and the means of binding of low molecular weight substrates such as BG, it may therefore be possible to design compounds that are able to fit into the active site and inactivate even the mutant AGTs. The CHO cell lines expressing these mutant AGTs will be useful for the screening of such inhibitors for their ability to sensitize cells to BCNU.

It should be noted that the control AGT and the mutant AGTs were expressed from the CMV promoter in our experiments. This is a very strong promoter in CHO cells and the amount of AGT formed was considerably greater than that found in most if not all human tumors. It is possible that the high level of AGT expression contributes to the insensitivity to BG. It is conceivable that both a mutation to a resistant form of AGT and a change in the level of AGT expression will be necessary to impart a high level of resistance to the BCNU/BG combination reducing the likelihood that such changes will be a problem in clinical trials. Nevertheless, it seems prudent to design strategies to overcome such resistance. The concentrations of BCNU used in the present experiments were considerably higher than those likely to exist in patients treated with this drug and much lower levels of expression of AGT may be sufficient to provide protection from chloroethylating agents in clinical protocols.

Finally, it is noteworthy that with cells expressing either the control or the mutants AGT, the concentration of BG or 5-nitroso-BP needed to get maximal enhancement of killing by BCNU is much higher than that needed to give >90% inactivation of the AGT. Similar results have been observed with a variety of human tumor cells treated with BG (Dolan, et al., 1990, *Proc. Natl. Acad. Sci. U.S.A.* 87: 5368–5372; Dolan, et al., 1991 *Cancer Res.* 51: 3367–3372; Marathi, et al., 1993, *Cancer Res.* 53: 4281–4286) or other derivatives (Pegg, et al., 1995, *Biochem. Pharmacol.* 50: 1141–1148). The reasons for this are not known with certainty but two possibilities are that: (a) a small amount of residual AGT may provide significant protection or (b) it is may be necessary to ensure that the AGT made de novo over the entire period in which lethal cross links can be formed from the $O^6$-chloroethyl guanine adducts reacts with BG rather than repairs DNA. This period may extend past the end of the 24 h period used in these experimental protocols and thus could involve a contribution from the residual drug present in the cells after the medium is changed. Furthermore, the competition would require more of the drug than the inactivation of AGT prior to treatment with the alkylating agent. It has been difficult to investigate this problem in detail with cells expressing the control AGT since the methods for assaying BG or derivatives currently available are not sufficiently sensitive to measure their intracellular levels in cultured cells and relate them to the biological effects and the sensitivity of the AGT in vitro. The use of the mutant AGTs in which much greater levels of BG are needed would move these levels into the measurable range and may provide a means to investigate this question.

7. EXAMPLE: EXPRESSION OF P156A AGT IN CD34+ HEMATOPOIETIC CELLS

7.1. MATERIAL AND METHODS

Retroviral Vectors—Retroviral vectors pMFGwtMGMT and pMFGΔMGMT were constructed by inserting the wild type and G156A mutant human MGMT cDNA coding sequences respectively, into the unique NcoI and BamHI restriction sites of the Moloney murine leukemia virus derived-retroviral vector pMFG (Ohashi et al. 1992, *Proc. Natl. Acad. Sci.* 89: 11332–11336). The NcoI and BamHI sites at the 5' and 3' termini of human MGMT cDNA sequence, respectively, were generated by PCR amplification with a pair of primers (5'-p:5° CTTGGAA CCATGGACAAGGATTGTGAAA3', (SEQ ID NO:2) 3'-p: 5'CTTAGGATCCCATCCGATGCAGTGTTACACG3' (SEQ ID NO:3): corresponding restriction sites underlined). The ATG sequence in the created NcoI site serves as start codon of human MGMT cDNA. ΔMGMT cDNA was generated by two steps of PCR amplification with the 5'-p and 3'-p primers and another pair or primers (5'-mp: 5'AGCGGAGCCGTGGCCAACTACTCCGGA3', (SEQ ID NO:4) 3'-mp: 5'TCCGGAGTAGTTGGCCACGGCTC-CGCTG3' (SEQ ID NO:5)). These primers were derived from the cDNA sequence with a single mismatch (bold) at the second base of codon Glycine 156 to Alanine. First, 5' and 3' fragments were amplified with primers 5'-p/3'-mp and 5'-mp/3'-3, respectively, then both 5' and 3' fragments were mixed to amplify the full length mutant cDNA with 5'-p and 3'-p primers. Sequences were confirmed by the dideoxynucleotide chain termination method (fmol DNA Sequencing System, Promega Biotec, Madison, Wis.).

Transfection of the vector constructs Into CHO cells—Six μg of each plasmid (pMFGwtMGMT and pMFGΔMGMT) were cotransfected into 1.8×10⁶ cells with 0.6 μg of pSV2neo plasmid DNA by Lipofectamine (Gibco BRL, Gaithersburg, Md.) following manufacturer's protocol. Clones of transfected cells were selected in G418 (1 g/L).

Virus producing cells—Virus producing cells lines were made by co-transfecting pMFGMGMT or pMFGΔMGMT and pSV₂neo DNA into the packaging of line GP+E86. After selection in G418, viral supernatant was collected and used to infect the amphotropic cell line GP+envAm12 (kindly provided by Arthur Bank, Columbia Univ). To increase titer, a supernatant "ping-pong" method was used as previously described (Bodine, 1990, *Proc. Natl. Acad. Sci.* 87: 3738). The amphotropic ψCRIP MFG-lacZ was kindly provided by Paul Robbins (Univ of Pittsburgh). Titer was estimated from supernatants collected after 6 daily media changes by infecting 1×10⁵ K562 cells (as described below) with limiting dilutions of viral supernatant.

K562 Transduction—The human chronic myelogenous leukemia cell line K562 was transduced as follows. At 80% confluence, amphotropic vMGMT and vΔMGMT producer cells were treated with 10 μg/mL mitomycin C for 2 hours, washed 4 times in serum-containing medium, trypsinized, and replated in complete medium. Twenty-four hours later, 2.5×10⁵/mL K562 cells were added along with human interleukin-3 (IL-3)(100 U/mL, kindly provided by Genetics Institute, Cambridge, Mass.), GM-CSF (100 U/ML, kindly provided by Sandoz Research Institute, Nutley, N.J.) and 6 μg/mL polybrene. Forty-eight hours later, the nonadherent K562 cells were procured and either analyzed for gene transfer or grown in medium containing 500 μg/mL G418. Selected cells were analyzed after 4 weeks.

CD34+ Transduction—Peripheral blood mononuclear cells were obtained by apheresis from patients treated with cyclophosphamide and G-CSF. CD34+ progenitors were isolated using the Ceprate SC Stem Cell Concentrator (Cell Pro, Bothell, Wash.) according to manufacturer's directions. Briefly, cells were washed and incubated with biotinylated anti-CD34 antibody, passed over an avidin column and the bound fraction eluted by gentle agitation. Recovered cells had an average purity of 57%. Freshly obtained CD34+ cells (5×10⁵ cells/ml) were resuspended in IMDM containing 20% heat inactivated FCS and supplemented with human SCF (100 mg/ml, Amgen), IL-3 (100 U/ml) and IL-6 (100 U/ml both from Sandoz) and protamine sulfate (4 mg/ml, Sigma) and co-cultured with MFG-ΔMGMT and MFG-lac producers prepared as above. At 48 hours, half of the media was removed, cells were pelleted and resuspended in fresh, supplemented media, and non-adherent cells were collected at 96 hours.

In vitro BCNU/BG treatment—Cells transduced with MFG-ΔMGMT, MFG-wtMGMT, MFG-lac or uninfected cells were incubated in serum free media containing 100 U/ml GM-CSF with or without 10 μM BG and incubated at 37° C. for 1 hour with continuous mixing. BCNU was dissolved in 100% ethanol and diluted to 10 mM with serum free media and immediately added to the cells. Following a two hour incubation at 37° C., cells were incubated in methylcellulose (Stem Cell Technologies, Inc.) containing either SCF, IL3, hemin, erythropoietin, GM-CSF (for CD34+ cells) or GM-CSF and IL-3 (for K562 cells) in triplicate. Cells treated with BG received an additional 5 μM dose in the methylcellulose medium. After incubation for 7–10 days at 37° C. colonies were enumerated and survival was analyzed at each BCNU dose.

Immunoassay—Cytospin preparations were stained for AGT using the monoclonal antibody mT3.1 (kindly provided by D. Bigner) and the biotin/avidin horseradish peroxidase system (Vector Laboratories, Burlingame, Calif.). Western blots were done by sonicating and boiling a sample in a buffer containing 50 mmol/L TRIS-HCL, pH 6.3.2% sodium dodecylsulfate (SDS), 1% β-mercaptoethanol, 0.1 mol/L dithiothreitol (DTT), 5% sucrose, and 300 μmol/L NaO₂ thovanadate. Total protein was quantitated by a modified Bradford assay (Bio-Rad Laboratories, Hercules, Calif.), and 30 to 50 μg of denatured protein was separated by SDS-polyacrylamide gel electrophoresis (SDS-PAGE) and electroblotted onto immobilon PC (S&S, Keene, N.H.). Human alkyltransferase was detected using the monoclonal antibody (MoAb)MT3.1 (kindly provided by D. Bigner and T. Brent). Signal was detected using a goat-antimouse IgG conjugated to horseradish peroxidase and developed via chemiluminescence using the ECL kit from Amersham according to the manufacturer's instructions. The human AGT was detected by immunostaining with the monoclonal antibody mT3.1 and horseradish peroxidase conjugated secondary antibody. Chemiluminescent signal was detected using the ECL kit (Amersham). AGT activity was correlated to densitometric band intensity using a standard curve generated from transduced K562 cells expressing high levels of MGMT.

AGT Assay—AGT activity was measured as [$^3$H]-methyl groups removed from [$^3$H] O$^6$-methylguanine present in [$^3$H]-methylnitrosourea treated alkylated calf thymus DNA. The alkylated [$^3$H-methyl] O$^6$methylguanine and N$^7$methylguanine bases were separated by HPLC and quantified by liquid scintillation. AGT activity was expressed as fmol O$^6$mG removed/µg DNA or fmol O$^6$removed/mgprotein.

PCR Provirus Analysis—DNA was isolated from single colonies selected from methylcellulose plates with a standard Proteinase K/Triton X-100 method. A 152 bp human MGMT fragment and a 290 bp human dystrophin fragment was amplified and the fragments were separated on a 2% agarose gel and detected by either ethidium bromide stain or Southern blot.

RT PCR Analysis—Purified total RNA or RNA prepared using the standard Proteinase K/Triton X-100 method was digested extensively with DNaseI according to manufacturer's instructions. Reverse transcription and PCR was performed using the RNA PCR kit (Perkin-Elmer-Cetus, Norwalk, Conn.). In the presence of reverse transcriptase, a 497 bp fragment was amplified using the sense primer (5'TGGTACCTCACCCTTACCGAGTC3'(SEQ ID NO:6)) containing sequences of MFG proviral backbone and the anti-sense primer (5'ACACCTGTCTGGTGAACGACTCT3'(SEQ ID NO:7)) specific to human MGMT.

Helper Virus Assay—Viral supernatants from amphotropic producer cells were used to transduce K562 and NIH 3T3 cells. Supernatants from these cells were then cocultured with fresh NIH 3T3 cells. The latter were then analyzed for the presence of proviral sequences by PCR and supernatants were used to infect the NIH lac cells. Since the latter contain proviral sequences, the presence of virus in the supernatant could be detected by supernatant transmission of lac + virus to naive NIH-3T3 cells. NIH 3T3 cells were cultured for one month at which time supernatant was reassayed for helper virus.

7.2. RESULTS

Figure 7A:
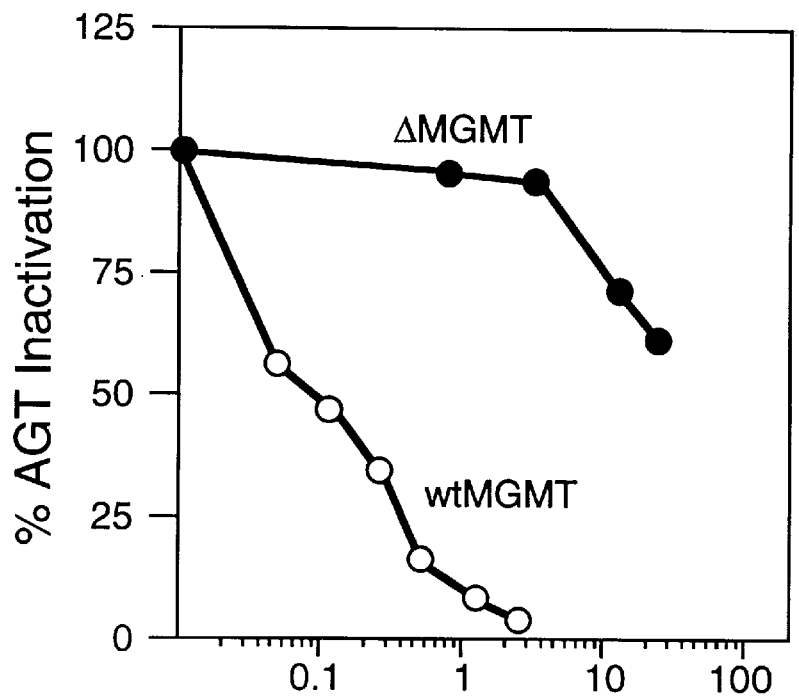
FIG. 7a and FIG. 7b show the effect of differing concentrations of BG on AGT activity for wtMGMT (AGT) and ΔMGMT for transduced CHO cells (FIG. 7a) and transduced CD34$^+$ cells (FIG. 7b).

Expression of AGT and BG resistance In CHO cells—ΔAGT activity was compared to wtAGT in transfected CHO cells by enzyme assay and western blot. AGT activity was 3.5 fmol/µg DNA in ΔMGMT transfected CHO cells compared to 84 fmol/µg DNA in wtMGMT transfectants. Differences in AGT activity were greater than the differences observed by western blot. However, there was comparatively more immunoreactive protein determined by western blot than suggested by AGT activity. In CHO cells, ΔAGT was much more resistant to BG than wtAGT. ΔMGMT transfected cells treated with 25 µM BG had an IC$_{50}$ for inhibition of AGT of approximately 30 µM compared to <0.1 µM for cells transfected with wtMGMT. (FIG. 7a).

Titer—MFG-ΔMGMT titer from Am-12 supernatant was estimated by immunohistochemical detection of infected K562 cells. A clone with a titer of 5×10$^5$ AGT positive cfu/ml was used for further experiments. Of note, AGT was nuclear, indicating that the mutant protein retained its nuclear localization.

Figure 7B:
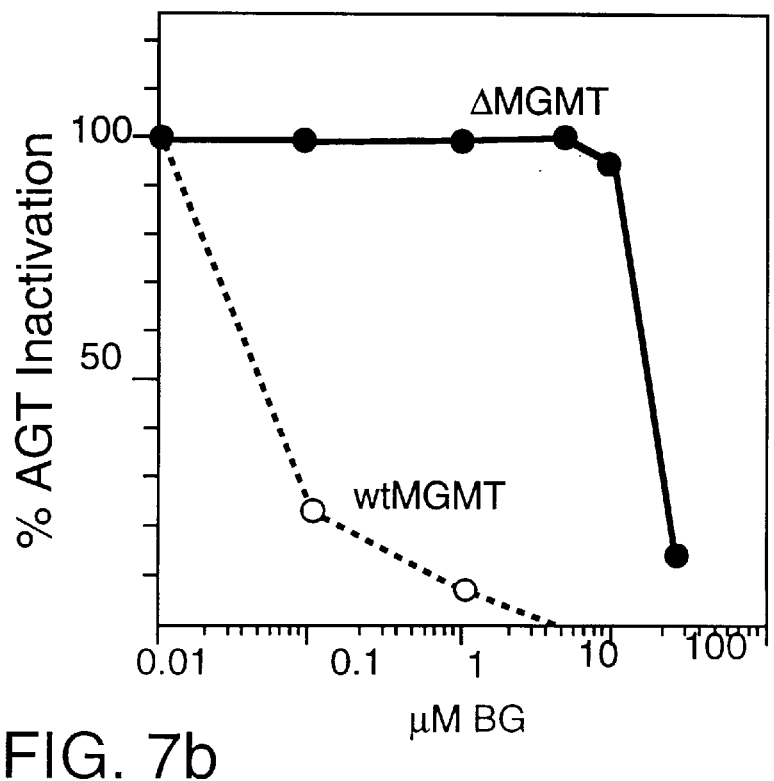
Figure 8B:
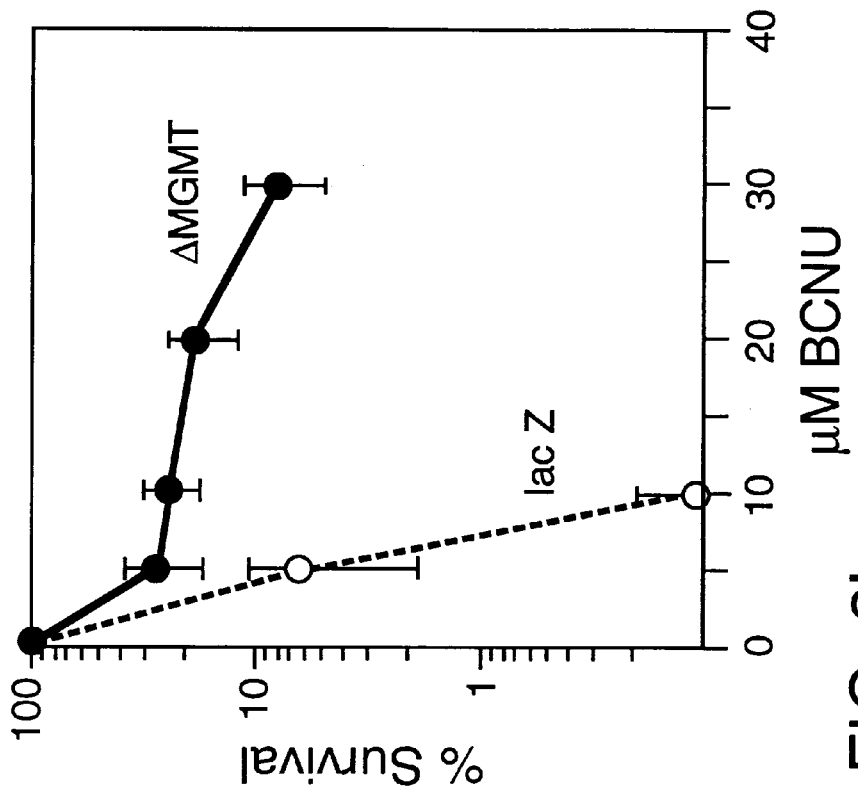
FIG. 8a and FIG. 8b show the effect of 10 μm BG and differing concentrations of BCNU on activity of the G156A mutant (ΔAGT) (●), wild type AGT (wtMGMT) (○) and untransduced control for K562 cells (FIG. 8a) and CD34$^+$ cells (FIG. 8b).
Figure 8A:
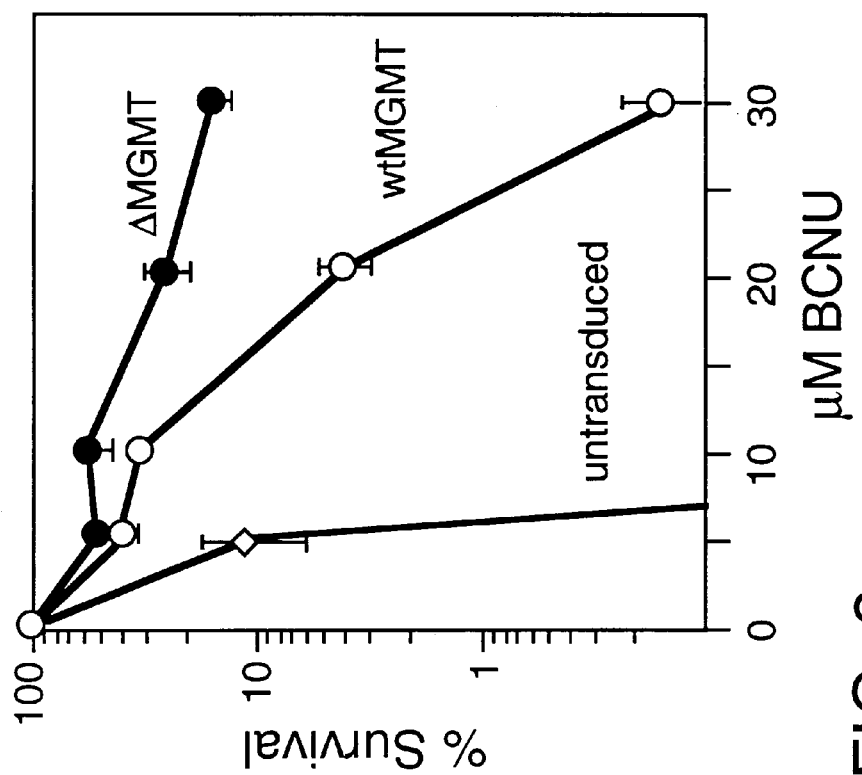

Expression and Drug Resistance In K562 cells—K562 cells were retrovirally infected by co-culture with wtMGMT or ΔMGMT Am-12 producer cells. AGT activity and resistance to BG were compared in the two cell cultures without prior selection. Mean AGT levels were 25.7 fmol/µg DNA in wtMGMT transduced cells, 2.7 fmol/µg DNA in ΔMGMT transduced cells and 0 fmol/µg DNA in uninfected cells. The IC$_{50}$ for BG inactivation of AGT was <0.1 µM compared to approximately 18 µM In wt and ΔMGMT transduced cells respectively. At 5 µM BG ΔAGT containing cells retained >90% activity while wtAGT was undetectable (FIG. 7b). To determine whether ΔAGT expression could increase tolerance to BG and BCNU, transduced K562 cells were exposed to 10 µM BG and various concentrations of BCNU and plated in methylcellulose. Clonogenic ΔMGMT transduced cells were significantly more resistant to the drug combination than wtMGMT transduced and untransduced cells (FIG. 7a). The BCNU IC$_{50}$ was 11.3 vs 4 vs 1.3 µM and the IC$_{90}$ was >30 vs 16 vs 5 µM, for ΔMGMT, wtMGMT and untransduced cells, respectively. Furthermore, ΔMGMT cells maintained 20% clonogenic survival at 30 µM BCNU & BG compared to <1% of cells transduced with wtMGMT. To assess proviral integration, individual colonies were subjected to PCR analysis and a 152 bp MGMT fragment was amplified in 22 of 33 colonies (67%). AGT immunoreactive protein detected in pooled colonies from wtMGMT infected cells was 10 fold higher than in colonies from ΔMGMT transduced cells.

Expression and Drug Resistance in human CD34$^+$ cells—The non-adherant cell count in co-cultures of human CD34$^+$ cells and MFG-ΔMGMT or MFG-lac producers increased 5-fold over 96 hours. After co-culture, cells were treated with BCNU alone or with BG and plated in methylcellulose. ΔMGMT transduced CD34$^+$ cells had only a small increase in resistance to BCNU alone compared to lac Z transduced cells. However, after pretreatment with 10 µM BG to deplete wtAGT, a striking resistance to BCNU was observed in ΔMGMT transduced CD34$^+$ cells (FIG. 7b). The divergence between the lac Z transduced and ΔMGMT transduced clonogenic progenitor cell survival increased as the dose of BCNU increased. Thus, relative to the survival of cells transduced with lac Z, the survival of ΔMGMT was 73.7±10.6 at the IC$_{50}$ 49.0±24.2 at the IC$_{90}$ and approximately 25% were resistant to 10 µM BG and 10 µM BCNU, a dose which killed greater than 99% of lac Z transduced hematopoietic progenitor cells. Individual progenitor colonies (BFU-E and CFU-GM) were analyzed for proviral integration and efficiency of transduction was 76% as determined by PCR. ΔMGMT mRNA expression was detected in pooled colonies by RT-PCR. AGT levels detected by western blot were 5 fold higher in ΔMGMT pooled progenitor colonies than lac progenitors and enzyme activity was increased 2 fold.

A drug resistance gene selectively expressed in hematopoietic cells may provide a distinct therapeutic advantage during chemotherapy exposure for the treatment of cancer. This shows the utility of ΔAGT as a mutant drug resistance protein, resistant to inactivation by BG and is thus capable of protecting cells from the combination of BG and BCNU. We have shown that the retroviral vector MFGΔMGMT transmits ΔAGT expression into K562 cell lines and into human CD34$^+$ cells. These cells become remarkably resistant to the combination of BG & BCNU compared to cells expressing wtAGT at higher levels.

Other disclosures regarding studies with cell lines which lack endogenous expression of AGT and are normally quite sensitive to BCNU have shown that overexpression of MGMT results in resistance to BCNU. CD34+ cells express low but detectable levels of AGT and are more resistant to BCNU than these cell lines. Transduction of CD34+ cells with wtMGMT had little effect on BCNU resistance furthermore, both CD34+ cells and tumor cell lines with very high levels of wtAGT activity can be sensitized to BCNU after inactivation of AGT by BG. The combination of BG treatment with ΔMGMT gene transfer shows the feasibility of selectively protecting hematopoietic cells during systemic treatment with the BG & BCNU combination to an even greater extent than overexpression of MGMT would protect these cells from BCNU alone.

In contrast to gene transfer of wtMGMT into CD34+ cells, transduction of ΔMGMT into CD34+ cells resulted in marked enhancement of clonogenic survival after BG and BCNU. These results relied on efficient gene transfer into CD34+ derived colonies (over 70%). Over 30% of colonies appeared very resistant to BG & BCNU. These data show that the ΔMGMT cDNA is a better candidate drug resistance gene than wtMGMT because the relative protection seen with ΔMGMT and BG and BCNU is much greater than we observed with wtMGMT and BCNU alone at similar levels of gene expression. It is possible that higher expression of MGMT in human CD34+ cells would partially protect cells from BG & BCNU as was observed with K562 cells. However, this is unlikely because transduction of cells expressing endogenous AGT results in less enhancement of BCNU resistance as originally seen and because the protection noted after wtMGMT gene transfer gene into murine hematopoietic cells was modest as well. Allay, et al. (1995, *Blood* 85: 3342–3351) and Harris, et al. (1995, *Proc. Amer. Assoc. Can. Res.* 36: 419) have found less than a 2 fold increase in BCNU resistance after retroviral mediated gene transfer of wtMGMT. In contrast, these data results indicate remarkable protection to cells expressing ΔMGMT and treated with BG & BCNU.

Another approach described by Harris (1995, *Proc. Amer. Assoc. Can. Res.* 36: 419) is transfer of the bacterial ada gene into murine hematopoietic progenitors. These authors noted increased resistance to BG and BCNU in vivo. The degree of resistance was not as high as disclosed in this example even though the bacterial protein is more resistant to BG than the ΔMGMT protein. Three caveats may explain the differences. First, there is evidence that the bacterial protein is not well nuclear localized and may not be an efficient DNA repair protein even if overexpressed. Second, mouse AGT has a higher $IC_{50}$ for BG than human AGT so that mouse cells are more resistant to the combination of BG & BCNU than human cells. Consequently, the degree of protection noted can not be directly converted to that expected in human CD34+ cells. Third, regarding in vivo applications, there is a significant possibility that an immune response would develop against the bacterial AGT that would not be expected following introduction of ΔAGT, with only a single amino acid change, into cells in vivo.

This example does not directly show gene transduction into cells more primitive than the BFU-E. While targeting such primitive cells is within the scope of the present invention, transduction of very early progenitors may not be a prerequisite for successful introduction of this gene into humans for the purpose of protection from myelosuppression. Most chemotherapeutic regimens are administered for 2–6 months, suggesting that this would be the time window needed for persistent gene expression. While our earlier murine studies document gene expression out to 1 year, successful gene therapy may involve techniques that transduce CD34+ cells which, because of their state of differentiation repopulate the human marrow after every treatment cycle, contributing to hematopoiesis for a period perhaps as short as 1–6 months. After this if there is loss of the transduced cells due to entrance of more committed progeny into the cycle, it would not impact on treatment with other agents or patient outcome. ΔMGMT expressing cells might be significantly enriched with each cycle of drug treatment even if only a small proportion of cells are initially transduced, ameliorating the myelosuppression and preventing cumulative toxicity.

Furthermore, since use of nitrosoureas and other agents which attack at $O^6$ of guanine may be associated with cumulative myelosuppression and eventual secondary leukemias, it may be postulated that after ΔMGMT gene therapy, these cells can be protected directly by gene transduction or indirectly by maintenance of a higher white count, decreasing the stimulus for their proliferation.

Use of MGMT as a drug resistance gene in CD34+ cells is fundamentally different than the use of other genes for this purpose. MDR is expressed at moderately high levels in early hematopoietic progenitors although overexpression has been shown to increase drug resistance of CD34+ cells in vitro. Likewise, aldehyde dehydrogenase is expressed at high levels in early hematopoietic progenitors generating a relative resistance to cyclophosphamide. Overexpression of DHFR protects cycling cells but there is no evidence that it protects early progenitors. In contrast, AGT is expressed at low levels in early hematopoietic progenitors and these cells are susceptible to cumulative cytotoxicity and secondary transformation into leukemia. The overexpression of MGMT protects against both of these events.

The G156A AGT mutant appeared less active than the wt protein in CHO cells, K562 and normal CD34+ cell cultures based on a comparison of the levels of immunoreactive protein to enzyme activity. While this difference was quite pronounced in the cell lines it was present to a much less extent in the normal CD34+ cells. The mutant protein may be less stable than the wt protein. Perhaps it fails to maintain its active conformation or perhaps the inactive form is not degraded through the ubiquitin pathway as rapidly as the wt protein. In fact, finding the ΔAGT to be such potent protection from cytotoxicity from BG & BCNU is all the more remarkable because of the relatively low levels of enzyme activity in both the cell lines and the CD34+ cells.

Therefore, overexpression of ΔMGMT transmits resistance to the chemotherapeutic combination BG & BCNU, providing a greater therapeutic advantage than does transduction of the wtMGMT protect against BCNU alone. This, plus the continued successful development of BG in clinical trials to potentiate the efficacy of BCNU in the treatment of cancer, show that gene therapy with ΔMGMT as disclosed throughout this specification will provide significant, selective protection of hematopoietic cells in the clinical setting.

Whereas particular embodiments of this invention have been described above for the purposes of illustration, it will be evident to those persons of ordinary skill in the art that numerous variations of the details of the present invention may be made without departing from the invention as defined in the appended claims.

What is claimed is:

1. A method of inhibiting myelosuppression caused by chemotherapy in a mammalian host while leaving unaltered the malignant cells in said host, which comprises sequentially:

(a) collecting bone marrow cells from said host;

(b) transducing said population of bone marrow cells with a recombinant vector containing a nucleic acid sequence expressing a human mutant form of $O^6$-alkylguanine-DNA alkyltransferase, resulting in transduced bone marrow or bone marrow derived cells;

(c) administering to said host a chemotherapy regime, wherein said regime comprises use of one or more anti-neoplastic alkylating agents whose chemotherapeutic actions are impeded by $O^6$-alkylguanine-DNA alkyltransferase and an $O^6$-benzylated guanine compound, said guanine compound inactivating an $O^6$-alkylguanine DNA alkyltransferase protein but not mutant forms of $O^6$-alkylguanine-DNA alkyltransferase;

(d) introducing said transduced bone marrow cells into said mammalian host such that expression of said mutant protein confers resistance in said transduced cells to said $O^6$-benzylated guanine compound while leavig unaltered the wild type activity of the $O^6$-alkylguanine-DNA alkyltransferase in untransduced tumor cells; and (e) repeating the chemotherapy regime of step (c); wherein said transduced bone marrow cells are protected from cytotoxicity by said alkalating agents but the $O^6$-alkylguanine-DNA alkyltransferase in nontransduced malignant cells is inactivated by said $O^6$-benzylated guanine compound.

2. The method of claim 1 wherein said mammalian host is a human.

3. The method of claim 2 wherein said bone marrow cells are $CD34^+$ enriched cells from peripheral blood.

4. The method of claim 3 wherein said $O^6$-benzylated guanine derivative is $O^6$-benzylguanine.

5. The method of claim 3 wherein said recombinant vector is MFG-hAGT/P140A.

6. The method of claim 4 wherein said recombinant vector is MFG-hAGT/P140A.

7. The method of claim 3 wherein said recombinant vector is MFG-hAGT/G156A (ΔMGMT).

8. The method of claim 4 wherein said recombinant vector is MFG-hAGT/G156A (ΔMGMT).

9. A method of dominant selection of a second transduced gene in transduced cells which comprises:
   (a) transducing a first gene expressing a known AGT mutant resistant to an $O^6$-benzylated guanine derivative into target cells;
   (b) transducing a second gene into the target cells;
   (c) coculturing the transduced population of target cells in the presence of an $O^6$-benzylated guanine derivative and an alkylating or methylating agent; and
   (d) observing the clonogenic survival of the target cells in the presence of an $O^6$-benzylated guanine derivative and an alkylating or methylating agent, wherein surviving cells contain the second gene.

* * * * *